United States Patent
Rivier

(10) Patent No.: US 6,326,463 B1
(45) Date of Patent: *Dec. 4, 2001

(54) CYCLIC CRF AGONISTS

(75) Inventor: Jean E. F. Rivier, La Jolla, CA (US)

(73) Assignee: The Salk Institute For Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,889

(22) PCT Filed: May 27, 1998

(86) PCT No.: PCT/US98/10720

§ 371 Date: Nov. 29, 1999

§ 102(e) Date: Nov. 29, 1999

(87) PCT Pub. No.: WO98/54222

PCT Pub. Date: Dec. 3, 1998

Related U.S. Application Data

(63) Continuation-in-part of application No. 08/865,772, filed on May 30, 1997, now Pat. No. 5,824,771, which is a continuation-in-part of application No. 08/575,148, filed on Dec. 19, 1995, now Pat. No. 5,844,074, which is a continuation-in-part of application No. 08/353,928, filed on Dec. 12, 1994, now Pat. No. 5,663,292.

(51) Int. Cl.[7] .............................. A61K 38/28; A61K 38/12
(52) U.S. Cl. .............................. 530/306; 530/317; 514/2; 514/805; 930/21; 930/70; 930/260
(58) Field of Search .................... 530/306, 317; 930/21, 70, 260; 514/2, 805

(56) References Cited

U.S. PATENT DOCUMENTS

| | | | |
|---|---|---|---|
| 5,493,006 | 2/1996 | Miranda et al. | 530/306 |
| 5,510,458 | 4/1996 | Kornreich et al. | 530/306 |
| 5,663,292 | 9/1997 | Rivier | 530/306 |
| 5,824,771 | * 10/1998 | Rivier | 530/306 |
| 5,844,074 | 12/1998 | Rivier | 530/306 |

* cited by examiner

*Primary Examiner*—Michael Borin
(74) *Attorney, Agent, or Firm*—Fitch, Even, Tabin & Flannery

(57) ABSTRACT

Novel cyclic CRF agonist peptides have the amino acid sequence: (cyclo 30–33)Ac-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Glu-Ala-$R_{32}$-$R_{33}$-Asn-Arg-Lys-Leu-Nle-Glu-Ile-Ile-$NH_2$ wherein $R_{32}$ is His, D-His or an equivalent α-amino acid; $R_{33}$ is Lys or Orn. The N-terminus may be extended by Tyr, D-Tyr or Ile. Lys may be substituted for $Arg^{23}$, and its side chain connected by a lactam bridge to $Glu^{20}$ to form a bicyclic peptide. Certain disclosed CRF agonists include: (cyclo 30–33)[Ac-$Ser^7$, D-$Phe^{12}$, $Nle^{21,38}$, $Glu^{30}$, $Lys^{33}$]r/hCRF(7–41); (cyclo 30–33)[Ac-$Ser^7$, D-$Phe^{12}$, $Nle^{21,38}$, $Glu^{30}$, D-$His^{32}$, $Lys^{33}$]r/hCRF(7–41); (bicyclo 20–23, 30–33)[Ac-$Ser^7$, D-$Phe^{12}$, $Nle^{21,38}$, $Lys^{23,33}$, $Glu^{30}$, D-$His^{32}$]-r/hCRF(7–41); (cyclo 30–33)[Ac-$Ser^7$, D-$Phe^{12}$, $Nle^{18,21}$, $Glu^{30}$, D-$Ala^{32}$, $Lys^{33}$]α-helicale CRF(7–41); and (cyclo 30–33)[Ac-$Ser^7$, D-$Phe^{12}$, $Nle^{21,38}$, $CML^{27,40}$, $Glu^{30}$, $Lys^{33}$]r/hCRF(7–41). Labelled agonist such as (cyclo 30–33)[Ac-$I^{125}Tyr^6$, D-$Phe^{12}$, $Nle^{21,38}$, $Glu^{30}$, $Lys^{33}$]r/hCRF(6–41) and (cyclo 30–33)[Ac-$I^{125}$D-$Tyr^6$, D-$Phe^{12}$, $Nle^{21,38}$, $Glu^{30}$, D-$His^{32}$, $Lys^{33}$]r/hCRF (6–41) are useful in screening for more potent CRF agonists.

12 Claims, No Drawings

CYCLIC CRF AGONISTS

This application is a continuation-in-part of Ser. No. 08/865,772, filed May 30, 1997 and now U.S. Pat. No. 5,824,771 which is a CIP of Ser. No. 08/575,148 filed Dec. 19, 1995 now U.S. Pat. No. 5,844,074 which is a CIP of Ser. No. 08/353,928 filed Dec. 12, 1994 now U.S. Pat. No. 5,663,292.

This invention is generally directed to peptides and to the pharmaceutical treatment of mammals using such peptides. More specifically, the invention relates to cyclic agonists of the hentetracontapeptide CRF which mimic the pharmacological properties thereof and are superior thereto in at least some aspects, to pharmaceutical compositions containing such cyclic CRF agonists, to methods of treatment of mammals using such cyclic CRF agonists, and to methods of screening for new drugs using such peptides.

A physiologic corticotropin releasing factor (CRF) was first characterized from the ovine species (oCRF) in 1981. As disclosed in U.S. Pat. No. 4,415,558, oCRF (SEQ ID NO:1) was found to be a 41-residue amidated peptide which lowers blood pressure in mammals when injected peripherally and stimulates the secretion of ACTH and β-endorphin.

In about 1981, a 40-residue amidated peptide was isolated from the skin of the South American frog *Phyllomedusa sauvagei* and referred to as sauvagine. Sauvagine (SEQ ID NO:3) has an amino acid sequence homologous to ovine CRF, having been characterized by Erspamer et al. and described in *Regulatoy Peptides*, Vol. 2 (1981), pp. 1–13. When given intravenously (iv), sauvagine and OCRF cause vasodilation of the mesenteric arteries so as to lower blood pressure in mammals and also stimulate the secretion of ACTH and β-endorphin. However, when administered intracerebroventricularly(icv), there is an elevation of heart rate and mean arterial blood pressure, which are secondary to activation of the sympathetic nervous system.

Rat CRF (rCRF) (SEQ ID NO: 2) was later isolated, purified and characterized; as described in U.S. Pat. No. 4,489,163, it was found to be homologous, having 7 amino acid differences from oCRF. The amino acid sequence of human CRF was determined to be the same as that of rCRF. rCRF and hCRF are used interchangeably, with the designation r/hCRF being frequently used.

Peptides generally homologous to oCRF, i.e. about 54% homology, were isolated from the urophyses of different species of fish and were termed Urotensin I (UI). One is referred to as sucker fish(sf) urotensin, being described in an article by Lederis et al., *Science* Vol. 218, No. 4568, 162–164 (Oct. 8, 1982). A homolog, carp urotensin, is described in U.S. Pat. No. 4,533,654.

Another urotensin was later isolated from the urophyses of Flathead (Maggy) Sole; it is sometimes referred to as Maggy urotensin and is described in U.S. Pat. No. 4,908, 352. Synthetic UIs have been found to also stimulate ACTH and β-endorphin activities.

Since the original discoveries of CRFs in mammals and urotensins in fish, CRFs have now been shown to exist in other animal species. For example, fish CRF was found to be a 41-residue peptide having high homology to r/hCRF; it is described in an article by Lederis et al. that appears at pages 67–100 in *Fish Physiology* (ed. Farrell), Academic Press, San Diego, 1994). Synthetic fish CRF (fCRF) stimulates ACTH and β-endorphin activities in vitro and in vivo and has similar biological activities to mammalian CRFs. These various CRFs and urotensins, along with sauvagine are considered to form a larger family of CRF-like peptides and analogs.

One such CRF analog having a high alpha-helical forming potential was developed in about early 1984. This 41-residue amidated peptide is referred to as AHC (alpha-helical CRF) (SEQ ID NO: 4) and is described in U.S. Pat. No. 4,594,329. Other CRF analogs containing D-isomers of α-amino acids were developed, such as those shown in U.S. Pat. No. 5,278,146. Synthetic r/hCRF, oCRF and AHC all stimulate ACTH and β-endorphin-like activities (β-END-Li) in vitro and in vivo and substantially lower blood pressure when injected peripherally. Biopotent cyclic CRF analogs are disclosed in U.S. Pat. No. 5,493,006 (Feb. 20, 1996) and in WO 96/18649 which discloses cyclizing the molecule by creating an amide bond between the sidechains of the residues in positions 30 and 33.

During the search for improved analogs of CRF, it was determined that the first three residues at the N-terminus of the native CRF molecule, namely the residues located N-terminally of the Pro-Pro dipeptide, could be deleted without significantly changing the molecule's potency as a CRF agonist. Such analogs are commonly referred to using the shorthand nomenclature CRF(4–41); thereafter, such N-terminally shortened analogs were frequently used to shorten laboratory syntheses. Furthermore, it is indicated in the '329 patent mentioned above that such analogs retain substantial biopotency as a CRF agonist even if one or both of the proline residues were also deleted, although there would be a significant reduction from the potency of the comparable CRF(4–41) analog. At about the same time, it was disclosed in U.S. Pat. No. 4,605,642 that deletion of the first 8 or 9 N-terminal residues created potent CRF antagonists, i.e. CRF(9–41) and CRF(10–41), and it was furthermore disclosed that some antagonistic activity was also shown by CRF(8–41), which is created when only the first 7 residues at the N-terminus are deleted.

The numbering of the individual residues that is used throughout this application is based upon the structure of the native peptide of which the compound in question is an analog. For example, with respect to analogs of the 41-residue peptide rat/human CRF, the numbering of the particular amino acid residues in the native peptide is retained even though the N-terminus of the CRF analog is shortened by elimination of a sequence of residues.

Since the foregoing discoveries, the search for improved CRF agonists has continued.

Cyclic analogs of this CRF family of peptides have now been discovered which exhibit longer lasting and improved biological activity. It is shown that any of the members of the family of CRF-like peptides can be modified to create highly biopotent CRF agonists that bind strongly to the known CRF receptors and activate the CRF receptors.

The CRF family is considered to encompass those peptides which bind to the CRF receptors and have at least about 45% amino acid structural homology with ovine CRF, the first mammalian CRF isolated and characterized. The CRF family includes, but is not limited to, the following known peptides: ovine CRF (SEQ ID NO: 1), rat/human CRF (SEQ ID NO: 2), porcine CRF (SEQ ID NO: 5), bovine CRF (SEQ ID NO: 6), fish CRF (SEQ ID NO: 3), α-helical CRF(AHC) (SEQ ID NO: 4), carp urotensin (SEQ ID NO: 8), sucker urotensin (SEQ ID NO: 9), maggy urotensin (SEQ ID NO: 10), flounder urotensin (SEQ ID NO: 11), and sauvagine (SEQ ID NO: 4). Modifications in these molecules to incorporate a cyclizing bond, preferably a lactam, to join the side chains of the residues that are located as the 8th and 11th residues from the C-terminal residue, e.g. (cyclo 30–33)[Glu$^{30}$, Lys$^{33}$]r/hCRF, and to optionally also incorporate a D-isomer, preferably a residue of a basic or aromatic amino acid, as the residue which is the 9th residue from the C-terminal residue, e.g. (cyclo 30–33)[Glu$^{30}$, D-His$^{32}$, Lys$^{33}$]-r/hCRF, are known to increase biopotency.

It has now surprisingly been found that the synthesis of N-terminally shortened versions of such cyclic CRF analogs which are minus the first six residues (or the equivalent) compared to the respective CRF family member, i.e. creating a CRF(7–41) molecule or the like, results in the creation of unexpectedly potent CRF agonists when such shortened N-terminus is N-acylated. Surprisingly, such acylation of the a-amino group at such a truncated N-terminus i.e. which is now occupied by the 7-position residue of most CRF family members, in combination with the cyclizing linkage between the side chains of the 30 and 33-position residues, creates unexpectedly biopotent CRF agonists, which can be more potent than the comparable cyclic 41-residue analog. This is in dramatic contrast to comparable linear CRF(6–41) analogs which are only very weak agonists and to comparable linear CRF(8–41) analogs which are weak antagonists.

Basically, one preferred class of CRF agonist peptides is identified by the following general formula:

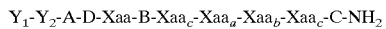

wherein $Y_1$ is an acyl group having not more than 15 carbon atoms; $Y_2$ is Tyr, D-Tyr, Ile or desY$_2$, A is Ser-Leu-Asp-Leu-Thr or Ser-Ile-Asp-Leu-Ser or Ser-Ile-Asp-Leu-Thr; D-Xaa is D-Phe, D-2Nal or D-Leu; B is a sequence of 17 amino acid residues that is found between Phe in the 12-position and Gln in position-30 of r/hCRF or the corresponding sequence of another peptide of the CRF family; Xaa$_c$ represent a pair of amino acid residues, the side chains of which are linked in a cyclizing bond; Xaa$_a$ is a natural α-amino acid residue other than Cys; Xaa$_b$ is a residue of either (a) a D-isomer amino acid from the group consisting of D-isomers of natural α-amino acids other than Cys and unnatural aromatic α-amino acids, or (b) a natural L-isomer α-amino acid; and C is a sequence of the last 8 amino acid residues of the C-terminal portion of a peptide of the CRF family; provided that Nle or Leu may be substituted for Met in B and in C. Additional substitutions such as are presently well known in the field of CRF agonists may also be made in these modified cyclic peptides, e.g. the substitution of Met by Nle or Leu.

These CRF agonists have a cyclizing bond between the residues in the 30- and 33-positions, and they may optionally have a second such bond between the residues in the 20- and 23-positions. These bonds are preferably each an amide bond (i.e. a lactam bridge) between side chain carboxyl and amino groups. Most preferably, there is a lactam bridge between a side chain carboxyl group on the residue in the 30-position, preferably Glu, and a side chain amino group on the 33-position residue, preferably Lys or Orn. Although a D-isomer may be present in position-32, one of the naturally occurring residues of the CRF-like family may also be present in the position (which corresponds to the 32-position of CRF), i.e. His, Gly, Leu, Gln and Ala; moreover, any α-amino acid is tolerated here. It may be preferable that a basic and/or aromatic D-isomer residue or its equivalent in this position in the region between the residues joined by this lactam bridge, e.g. D-His, D-Arg, D-Tyr, D-Nal, D-Pal, D-Aph, D-Agl(Nic), D-Orn, D-Dbu, D-Dpr, D-Orn(Nic) or imBzlD-His. Examples of other suitable residues (in addition to those mentioned above) include D-Ala, D-Glu, D-Asn, Aib, Asn, Pal, Nal, Phe and Tyr. In some instances, either D-His, D-Arg, D-Pal, D-Aph, or D-2Nal may be particularly preferred in the 32-position. When the second cyclizing bond option is incorporated, a lactam bridge between Glu in the 20-position and Lys in the 23-position is most preferred, and a D-isomer may also be optionally included in the 22-position. When the second lactam bridge is not included, D-Glu may be substituted in the 20-position.

These CRF agonists preferably have D-Phe, D-2Nal or D-Leu in the 12-position or an equivalent D-isomer, e.g. D-Cpa, D-Tyr, or D-3Pal, and norleucine or Leu is preferably substituted for any naturally occurring Met, e.g. in the 21 and 38 positions. Ac-Tyr, Ac-D-Tyr or Ile may be added at the N-terminus; the presence of tyrosine facilitates labeling by radioiodination. When radioiodination is to be accomplished, it may be preferable to substitute Asn, D-Asn or D-Ala for either His$^{32}$ or D-His$^{32}$, and to substitute Arg for Lys$^{36}$; they are generally considered to be structural equivalents which may be more stable. Other optional substitutions may also be made throughout the molecule as previously taught, and these are considered to create functional equivalents of the specific peptides described hereinafter.

In one preferred subgenus of cyclic agonists, the Leu residue in the 27-position is substituted with a methyl group on its α-carbon atom, i.e., CML. In addition to the preferred CML$^{27}$, at least one other CML residue is preferably also included in the CRF analog; for example, at one or more of positions 10, 14, 15, 17, 18, 19, 21, 24, 36, 37, 38, 40 and 41. Of these CML$^{14}$, CML$^{18}$, CML$^{37}$ and CML$^{40}$ are more preferred; and most preferred is such an agonist having CML$^{27,40}$. In an alternative subgenus, along with CML$^{27}$, Aib is included at least one of positions 22, 24, 28, 29, 31, 32, 34, 39, 40, and 41. Such other substitutions may further enhance biopotency and/or to increase duration of action, but their effect is less than that of the combination of the 30–33 side chain bridge with the deletion of the first six residues of the 41-residue peptide plus the acylation of the N-terminus.

Pharmaceutical compositions in accordance with the invention include such CRF agonists, or nontoxic addition salts thereof that are dispersed in a pharmaceutically acceptable liquid or solid carrier. The administration of such peptides or pharmaceutically acceptable addition salts thereof to mammals, particularly humans, in accordance with the invention may be carried out for the regulation of secretion of ACTH, β-endorphin, β-lipotropin, corticosterone and other products of the pro-opiomelanocortin (POMC) gene and corticosterone and/or for lowering blood pressure or increasing coronary flow and/or decreasing swelling and inflammation and/or for affecting learning, mood, behavior, appetite, gastrointestinal and intestinal functions and autonomic nervous system activities.

The peptides may also be used for drug screening for even more potent CRF agonists which bind to and activate CRF receptors.

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine. In addition the following abbreviations are used: Orn=ornithine, Nle= norleucine, Nva=norvaline, Agl=aminoglycine, Abu=2-aminobutyric acid, Dbu=2,4-diaminobutyric acid, Dpr=2,3-diaminopropionic acid, Hly=homolysine, Har= homoarginine, CML=C$^α$CH$_3$-leucine; Aib=C$^α$CH$_3$-L-alanine or 2-aminoisobutyric acid; Nal=L-β-(1- or 2-naphthyl)alanine; Pal=L-β-(2-,3- or 4-pyridyl)alanine; Cpa=L-(2-, 3-, or 4-chloro)phenylalanine; Aph=L-(2-,3- or 4-amino)phenylalanine; Amp=(2-, 3- or 4-aminomethyl) phenylalanine; Iamp=isopropyl Amp; imBzlHis= imidazolebenzyl Histidine; Nic=3-carboxypyridinyl (or nicotinyl); Me=methyl; Et=ethyl; Ipr=isopropyl; Nph= naphthoyl and Flu=fluorenoyl.

One broad group of CRF agonists is defined by the following amino acid sequence (which group should be understood to include the equivalent nontoxic salts thereof) and is based upon substitution of residues at particular positions that have been shown to be permitted in the CRF family sequence without impairing CRF biopotency:

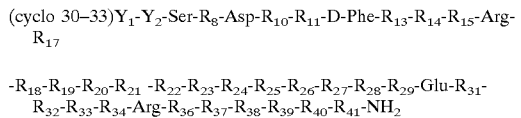

wherein $Y_1$ is an acyl group having not more than 15 carbon atoms; $Y_2$ is Tyr, D-Tyr, Ile or des$Y_2$; $R_8$ is Leu or Ile; $R_{10}$ is Leu or CML; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, CML, Nle or Met; $R_{19}$ is CML, Leu or Ile; R20 is Glu, D-Glu, Cys or His; $R_{21}$ is Nle, Leu, CML or Met; $R_{22}$ is Ala, D-Ala, Aib, Thr, Asp or Glu; $R_{23}$ is Arg, Cys, Orn or Lys; $R_{24}$ is Ala, Gln, Ile, Asn, CML or Aib; $R_{25}$ is Asp or Glu; $R_{26}$ is Gln, Asn or Lys; $R_{27}$ is CML, Glu, Gln or Leu; $R_{28}$ is Ala, Lys, Arg or Aib; $R_{29}$ is Gln, Aib or Glu; $R_{31}$ is Aib or an L-isomer of a natural α-amino acid other than Cys; $R_{32}$ is His, D-His, Aib or an L-or D-isomer α-amino acid other than Cys; $R_{33}$ is Lys or Orn; $R_{34}$ is Asn or Aib; $R_{36}$ is Lys, Orn, Arg, Har, CML or Leu; $R_{37}$ is CML, Leu, Nle or Tyr; $R_{38}$ is Nle, Met, CML or Leu; $R_{39}$ is Glu, Aib or Asp; $R_{40}$ is Ile, Aib, CML, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Phe may be substituted by Phe, Leu, Tyr, D-Leu, D-Tyr, D-Cpa, D-Trp, D-Nal, D-Pal or another D-isomer α-amino acid; provided that a second cyclizing bond may exist between $R_{20}$ and $R_{23}$. As an alternative to acylation at the N-terminus, a sulfonamide may be formed, or a sugar or a lipid can be added to modulate duration of action and solubility. As earlier indicated, there is wide latitude for selection of the residue in position-32, and examples of suitable additional residues for $R_{32}$ include the D- and L-isomers of Asn, Har, Arg, Nal, imBzlHis, Tyr, Ala, Leu, Val, Ser, Thr, Cpa, Pal, Lys, Phe and Gln, as well as Aib, Gly, D-Aph, D-Agl(Nic), D-Orn, D-Dbu, D-Dpr and D-Orn(Nic).

In another aspect, the invention provides CRF agonists having the following amino acid sequence (including nontoxic salts thereof):

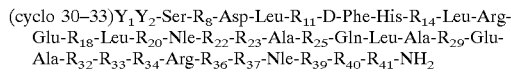

wherein $Y_1$ is an acyl group having not more than 7 carbon atoms; $Y_2$ is Tyr, D-Tyr, Ile or des$Y_2$; $R_8$ is Leu or Ile; $R_{11}$ is Thr or Ser; $R_{14}$ is Leu or CML; $R_{18}$ is Val, Nle, CML or Met; $R_{20}$ is Glu or D-Glu; $R_{22}$ is Ala or Thr; $R_{23}$ is Arg or Lys; $R_{25}$ is Asp or Glu; $R_{29}$ is Gln or Glu; $R_{32}$ is His, Aib, Ala, D-His, D-Arg, D-2Nal, D-Glu, D-Ala or a D-isomer of a natural amino acid other than D-Cys; $R_{33}$ is Lys or Orn; $R_{34}$ is Asn or Aib; $R_{36}$ is Lys or Leu; $R_{37}$ is Leu or CML; $R_{39}$ is Glu or Asp; $R_{40}$ is Ile, CML or Glu; and $R_{41}$ is Ile, Aib or Ala; wherein Phe may be substituted for D-Phe.

In a further aspect, the invention provides CRF agonists having the following amino acid sequence (including nontoxic salts thereof):

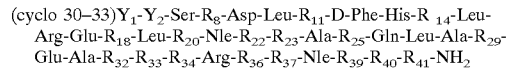

wherein $Y_1$ is an acyl group having not more than 7 carbon atoms; $Y_2$ is Tyr, D-Tyr, Ile or des$Y_2$; $R_8$ is Leu or Ile; $R_{11}$ is Thr or Ser; $R_{14}$ is Leu or CML; $R_{18}$ is Val, Nle, CML or Met; $R_{20}$ is Glu or D-Glu; $R_{22}$ is Ala or Thr; $R_{23}$ is Arg or Lys; $R_{25}$, is Asp or Glu; $R_{29}$ is Gln or Glu; $R_{32}$ is His, Ala, D-His, D-Arg, D-2Nal, D-Glu, D-Ala or a D-isomer of a natural amino acid other than D-Cys; $R_{33}$ is Lys or Orn; $R_{34}$ is Asn or Aib; $R_{36}$ is Lys or Leu; $R_{37}$ is Leu or CML; $R_{39}$ is Glu or Asp; $R_{40}$ is Ile, CML or Glu; and $R_{41}$ is Ile, Aib or Ala; wherein Phe may be substituted for D-Phe.

In yet another aspect, the invention provides CRF agonists having the following amino acid sequences (including nontoxic salts thereof):

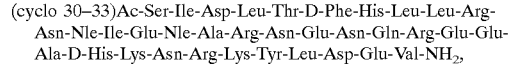

or

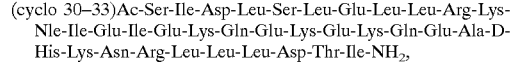

or

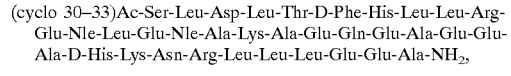

or

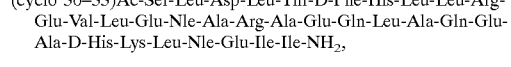

or

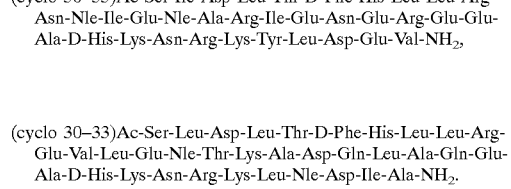

In still another aspect, the invention provides CRF agonists having the amino acid sequence (including nontoxic salts thereof):

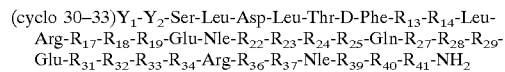

wherein $Y_1$ is a acyl group having not more than 7 carbon atoms; $Y_2$ is Tyr, D-Tyr, Ile or des$Y_2$; $R_{13}$ is His or Tyr; $R_{14}$ is Leu or CML; $R_{17}$ is Glu or CML; $R_{18}$ is Val, CML, Nle or Met; $R_{19}$ is Leu or CML; $R_{22}$ is Ala, Aib or Thr; $R_{23}$ is Arg or Lys; $R_{24}$ is Ala or Aib; $R_{25}$ is Asp or Glu; $R_{27}$ is Leu, CML or Glu; $R_{28}$ is Ala or Aib; $R_{29}$ is Gln, Aib or Glu; $R_{31}$ is Ala or Aib; $R_{32}$ is His, Ala, Aib, D-His or a D-isomer or L-isomer α-amino acid; $R_{33}$ is Lys or Orn; $R_{34}$ is Asn or Aib; $R_{36}$ is Lys, CML or Leu; $R_{37}$ is CML or Leu; $R_{39}$ is Glu, Aib or Asp; $R_{40}$ is Ile, Aib, CML or Glu; and $R_{41}$ is Ala, Aib, CML or Ile; and wherein D-Phe may be substituted by Phe, D-Tyr, D-Cpa, D-Nal or D-Pal.

In a still further aspect, the invention provides CRF agonists having the following amino acid sequence (including nontoxic salts thereof):

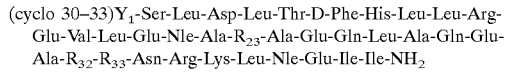

(cyclo 30–33)$Y_1$-Ser-Leu-Asp-Leu-Thr-D-Phe-His-Leu-Leu-Arg-Glu-Val-Leu-Glu-Nle-Ala-$R_{23}$-Ala-Glu-Gln-Leu-Ala-Gln-Glu-Ala-$R_{32}$-$R_{33}$-Asn-Arg-Lys-Leu-Nle-Glu-Ile-Ile-NH$_2$ wherein $Y_1$ is an acyl group having not more than 15 carbon atoms; $R_{23}$ is Arg or Lys; $R_{32}$ is His, Aib, D-His, D-Arg, D-Pal, D-Nal or a D-isomer or L-isomer of another natural amino acid other than Cys; $R_{33}$ is Lys or Orn; wherein D-Leu or D-2Nal may be substituted for D-Phe.

In a yet further aspect, the invention provides CRF agonists having the amino acid sequence (including nontoxic salts thereof):

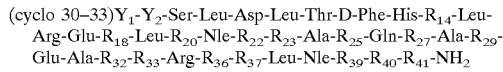

(cyclo 30–33)$Y_1$-$Y_2$-Ser-Leu-Asp-Leu-Thr-D-Phe-His-$R_{14}$-Leu-Arg-Glu-$R_{18}$-Leu-$R_{20}$-Nle-$R_{22}$-$R_{23}$-Ala-$R_{25}$-Gln-$R_{27}$-Ala-$R_{29}$-Glu-Ala-$R_{32}$-$R_{33}$-Arg-$R_{36}$-$R_{37}$-Leu-Nle-$R_{39}$-$R_{40}$-$R_{41}$-NH$_2$ wherein $Y_2$ is Tyr, D-Tyr, Ile or des$Y_2$; $R_{14}$ is Leu or CML; $R_{18}$ is Val, Nle, CML or Met; $R_{20}$ is Glu or D-Glu; $R_{22}$ is Ala, Aib or Thr; $R_{23}$ is Arg or Lys; $R_{25}$ is Asp or Glu; $R_{27}$ is Leu or CML; $R_{29}$ is Gln or Glu; $R_{32}$ is His or Ala; $R_{33}$ is Lys or Orn; $R_{34}$ is Asn or Aib; $R_{36}$ is Lys, CML or Leu; $R_{37}$ is CML or Leu; $R_{39}$ is Glu or Asp; $R_{40}$ is Ile, CML or Glu; and $R_{41}$ is Ile, CML, Aib or Ala.

In still another aspect, the invention provides CRF agonists having the amino acid sequence (including nontoxic salts thereof):

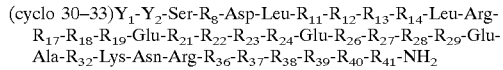

(cyclo 30–33)$Y_1$-$Y_2$-Ser-$R_8$-Asp-Leu-$R_{11}$-$R_{12}$-$R_{13}$-$R_{14}$-Leu-Arg-$R_{17}$-$R_{18}$-$R_{19}$-Glu-$R_{21}$-$R_{22}$-$R_{23}$-$R_{24}$-Glu-$R_{26}$-$R_{27}$-$R_{28}$-$R_{29}$-Glu-Ala-$R_{32}$-Lys-Asn-Arg-$R_{36}$-$R_{37}$-$R_{38}$-$R_{39}$-$R_{40}$-$R_{41}$-NH$_2$ wherein $Y_1$ is an acyl group having not more than 7 carbon atoms; $Y_2$ is Tyr, D-Tyr, Ile or des$Y_2$; $R_8$ is Leu or Ile; $R_{11}$ is Thr or Ser; $R_{12}$ is D-Phe or D-Leu; $R_{13}$ is His or Glu; $R_{14}$ is Leu or CML; $R_{17}$ is Glu, Lys or Asn; $R_{18}$ is Val, CML or Nle; $R_{19}$ is Leu or Ile; $R_{21}$ is Nle or Ile; $R_{22}$ is Ala or Glu; $R_{23}$ is Arg or Lys; $R_{24}$ is Ala, Asn, Gln or Ile; $R_{26}$ is Gln, Asn or Lys; $R_{27}$ is Leu, CML, Glu or Gln; $R_{28}$ is Ala, Arg or Lys; $R_{29}$ is Gln or Glu; $R_{32}$ is His, Gly, Aib, Ala, D-Ala, D-His or another aromatic D-isomer α-amino acid; $R_{36}$ is Lys, Arg, CML or Leu; $R_{37}$ is Leu, CML or Tyr; $R_{38}$ is Nle or Leu; $R_{39}$ is Glu or Asp; $R_{40}$ is Ile, Thr, CML or Glu; and $R_{41}$ is Ala, Ile, CML or Val.

In yet another aspect, the invention provides CRF agonists having the amino acid sequence (including nontoxic salts thereof):

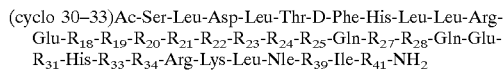

(cyclo 30–33)Ac-Ser-Leu-Asp-Leu-Thr-D-Phe-His-Leu-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-Glu-$R_{31}$-His-$R_{33}$-$R_{34}$-Arg-Lys-Leu-Nle-$R_{39}$-Ile-$R_{41}$-NH$_2$ wherein $R_{18}$ is Val or Nle; $R_{19}$ is CML, Leu or Ile; $R_{20}$ is Glu, D-Glu or Cys; $R_{21}$ is Nle or Met; $R_{22}$ is Ala, Aib or Thr; $R_{23}$ is Arg, Cys, Orn or Lys; $R_{24}$ is Ala or Aib; $R_{25}$ is Asp or Glu; $R_{27}$ is Leu or CML; $R_{28}$ is Ala or Aib; $R_{31}$ is Ala or Aib; $R_{33}$ is Lys or Orn; $R_{34}$ is Aib or Asn; $R_{39}$ is Glu or Asp; and $R_{41}$ is Ala or Ile; provided however that a second cyclizing bond may exist between $R_{20}$ and $R_{23}$.

In a yet further aspect, the invention provides CRF agonists having the amino acid sequence (including nontoxic salts thereof):

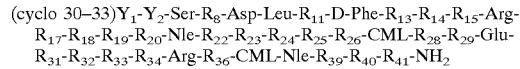

(cyclo 30–33)$Y_1$-$Y_2$-Ser-$R_8$-Asp-Leu-$R_{11}$-D-Phe-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-CML-$R_{28}$-$R_{29}$-Glu-$R_{31}$-$R_{32}$-$R_{33}$-$R_{34}$-Arg-$R_{36}$-CML-Nle-$R_{39}$-$R_{40}$-$R_{41}$-NH$_2$ wherein $Y_1$ is an acyl group having not more than 7 carbon atoms; wherein $Y_2$ is Tyr, D-Tyr, Ile or des$Y_2$; $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is D-Glu or Glu; $R_{22}$ is Ala, D-Ala, Aib, Thr, Asp or Glu; $R_{23}$ is Arg or Lys; $R_{24}$ is Ala, CML or Aib; $R_{25}$ is Asp or Glu; $R_{26}$ is Gln, Asn or Lys; $R_{28}$ is Ala or Aib; $R_{29}$ is Gln, Aib or Glu; $R_{31}$ is Ala or Aib; $R_{32}$ is His, D-His, Aib or another L-isomer or D-isomer α-amino acid; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Leu or Phe or Leu may be substituted for D-Phe.

In a still further aspect, the invention provides CRF agonists having the amino acid sequence (including nontoxic salts thereof):

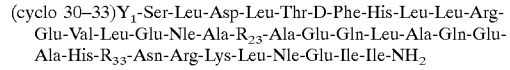

(cyclo 30–33)$Y_1$-Ser-Leu-Asp-Leu-Thr-D-Phe-His-Leu-Leu-Arg-Glu-Val-Leu-Glu-Nle-Ala-$R_{23}$-Ala-Glu-Gln-Leu-Ala-Gln-Glu-Ala-His-$R_{33}$-Asn-Arg-Lys-Leu-Nle-Glu-Ile-Ile-NH$_2$ wherein $Y_1$ is an acyl group having up to 7 carbon atoms; $R_{23}$ is Arg or Lys; $R_{33}$ is Lys or Orn.

In still another aspect, the invention provides CRF agonists having the amino acid sequence (including nontoxic salts thereof):

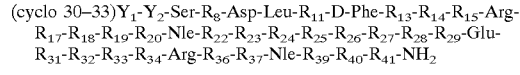

(cyclo 30–33)$Y_1$-$Y_2$-Ser-$R_8$-Asp-Leu-$R_{11}$-D-Phe-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-Glu-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein $Y_1$ is an acyl group having not more than 7 carbon atoms; wherein $Y_2$ is Tyr, D-Tyr, Ile or des$Y_2$; $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is D-Glu or Glu; $R_{22}$ is Ala, D-Ala, Aib, Thr, Asp or Glu; $R_{23}$ is Arg or Lys; $R_{24}$ is Ala or Aib; $R_{25}$ is Asp or Glu; $R_{26}$ is Gln, Asn or Lys; $R_{27}$ is Leu or CML; $R_{28}$ is Ala or Aib; $R_{29}$ is Gln, Aib or Glu; $R_{31}$ is Ala or Aib; $R_{32}$ is His, D-His, Aib, D-Arg, D-2Nal, D-3Pal, Gly, Tyr, D-Tyr, Ala, D-Ala or another aromatic D-isomer α-amino acid; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Leu or Phe or Leu may be substituted for D-Phe.

In yet another aspect, the invention provides CRF agonists having the amino acid sequence (including nontoxic salts thereof):

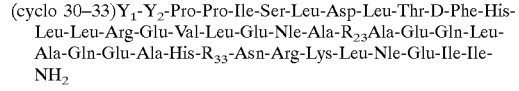

(cyclo 30–33)$Y_1$-$Y_2$-Pro-Pro-Ile-Ser-Leu-Asp-Leu-Thr-D-Phe-His-Leu-Leu-Arg-Glu-Val-Leu-Glu-Nle-Ala-$R_{23}$Ala-Glu-Gln-Leu-Ala-Gln-Glu-Ala-His-$R_{33}$-Asn-Arg-Lys-Leu-Nle-Glu-Ile-Ile-NH$_2$ wherein $Y_1$ is Ac; $Y_2$ is Tyr, D-Tyr, Ile or des$Y_2$; $R_{23}$ is Arg or Lys; $R_{33}$ is Lys or Orn; wherein His[32] may optionally be, and preferably is, substituted by D-His, D-Arg, D-Tyr, D-Nal, D-Pal, D-Asn, D-Lys, D-Aph, D-Phe, D-Cpa, D-Agl (Nic), imBzlD-His, D-Orn, D-Dbu, D-Dpr or D-Orn(Nic);

provided that a second cyclizing bond may exist between Glu$^{20}$ and R$_{23}$. Specific analogs of this group which are considered to be particularly biopotent from the standpoint of reducing blood pressure are:

cyclo(30–33)[Ac-Ser$^7$, D-Phe$^{12}$, Nle$^{21,38}$, Glu$^{30}$, Lys$^{33}$]r/ hCRF (7–41);

cyclo(30–33)[Ac-Ser$^7$, D-Phe$^{12}$, Nle$^{21,38}$, Glu$^{30}$, Orn$^{33}$]r/ hCRF (7–41);

cyclo(30–33)[Ac-D-Tyr$^6$, D-Phe$^{12}$, Nle$^{21,38}$, Glu$^{30}$, Lys$^{33}$]r/ hCRF (7–41);

cyclo(30–33)[Ac-Ser$^7$, D-Phe$^{12}$, Nle$^{21,38}$, Glu$^{30}$, D-His$^{32}$, Lys$^{33}$]r/hCRF(7–41); and cyclo(30–33)[Ac-Ser$^7$, D-Phe$^{12}$, Nle$^{21,38}$, Glu$^{30}$, D-2Nal$^{32}$, Orn$^{33}$]r/hCRF(7–41).

In a yet further aspect, the invention provides CRF agonists having the amino acid sequence (including nontoxic salts thereof):

(cyclo 30–33)Ac-Ser-Leu-Asp-Leu-Thr-D-Phe-His-R$_{14}$-R$_{15}$-Arg-R$_{17}$-Val-R$_{19}$-Glu-Nle-Ala-R$_{23}$-Ala-Glu-Gln-R$_{27}$-Ala-Gln-Glu-Ala-R$_{32}$-R$_{33}$-Asn-Arg-Lys-R$_{37}$-Nle-Glu-Ile-Ile-NH$_2$ wherein R$_{14}$, R$_{15}$, R$_{19}$, R$_{27}$ and R$_{37}$ are independently Leu or CML; R$_{17}$ is Glu or CML; R$_{23}$ is Arg or Lys; R$_{32}$ is D-His, D-Amp, D-Iamp, D-Arg, D-Asn, D-Tyr, D-Pal, D-Nal or another basic and/or aromatic D-isomer α-amino acid; R$_{33}$ is Lys or orn; wherein at least one of R$_{14}$, R$_{15}$, R$_{17}$, R$_{19}$, R$_{27}$ and R$_{37}$ is CML. Specific analogs of this group which are considered to be particularly biopotent from the standpoint of reducing blood pressure are:

cyclo(30–33)[Ac-Ser$^7$, D-Phe$^{12}$, Nle$^{21,38}$, CML$^{27}$, Glu$^{30}$, D-His$^{32}$, Lys$^{33}$]r/hCRF(7–41);

cyclo(30–33)[Ac-Ser$^7$, D-Phe$^{12}$, CML$^{15}$, Nle$^{21,38}$, Glu$^{30}$, D-Pal$^{32}$, Lys$^{33}$]r/hCRF(7–41);

cyclo(30–33)[Ac-Ser$^7$, D-Phe$^{12}$, CML$^{15}$, Nle$^{21,38}$, Glu$^{30}$, D-His$^{32}$, Lys$^{33}$]r/hCRF(7–41);

cyclo(30–33)[Ac-Ser$^7$, D-Phe$^{12}$, CML$^{14}$, Nle$^{21,38}$, Glu$^{30}$, D-His$^{32}$, Lys$^{33}$] r/hCRF(7–41);

cyclo(30–33)[Ac-Ser$^7$, D-Phe$^{12}$, Nle$^{21,38}$, Glu$^{30}$, D-His$^{32}$, Lys$^{33}$, CML$^{37}$]r/hCRF(7–41);

cyclo(30–33)[Ac-Ser$^7$, D-Phe$^{12}$, CML$^{17}$, Nle$^{21,38}$, Glu$^{30}$, D-His$^{32}$, Lys$^{33}$] r/hCRF(7–41); and cyclo(30–33)[Ac-Ser$^7$, D-Pro$^5$, D-Phe$^{12}$, CML$^{19}$, Nle$^{21,38}$, Glu$^{30}$, D-His$^{32}$, Lys$^{33}$]r/hCRF(7–41).

In still another aspect, the invention provides CRF agonists having the amino acid sequence (including nontoxic salts thereof):

(cyclo 30–33)Ac-Y$_2$-Ser-Leu-Asp-Leu-Thr-D-Phe-His-Leu-Leu-Arg-Glu-Val-Leu-Glu-Nle-Ala-R$_{23}$-Ala-Glu-Gln-Leu-Ala-Gln-Glu-Ala-His-R$_{33}$-Asn-Arg-Lys-Leu-Nle-Glu-Ile-Ile-NH$_2$ wherein Y$_2$ is Tyr, D-Tyr, Ile or desY$_2$; R$_{23}$ is Arg or Lys; R$_{33}$ is Lys or Orn; wherein D-Phe may be substituted by Phe, and wherein His$^{32}$ may optionally be, and preferably is, substituted by D-His, D-Amp, D-Iamp, D-Arg, D-Pal, D-Nal or a D-isomer of another natural amino acid other than Cys. Specific analogs of this group which are considered to be particularly biopotent from the standpoint of reducing blood pressure are:

cyclo(30–33)[Ac-Ser$^7$, D-Phe$^{12}$, Nle$^{21,38}$, Glu$^{30}$, D-His$^{32}$, Lys$^{33}$]r/hCRF(7–41);

cyclo(30–33)[Ac-Ser$^7$, D-Phe$^{12}$, Nle$^{21,38}$, GlU$^{30}$, D-His$^{32}$, Orn$^{33}$]r/hCRF(7–41);

cyclo(30–33)[Ac-Ser$^7$, D-Phe$^{12}$, Nle$^{21,38}$, Glu$^{30}$, D-2Nal$^{32}$, Lys$^{33}$]r/hCRF(7–41);

cyclo(30–33)[Ac-Tyr$^6$, D-Phe$^{12}$, Nle$^{21,38}$, Glu$^{30}$, D-His$^{32}$, Lys$^{33}$]r/hCRF(7–41); and cyclo(30–33)[Ac-Ser$^7$, D-Phe$^{12}$, Nle$^{21,38}$, Glu$^{30}$, D-3Pal$^{32}$, Lys$^{33}$]r/hCRF(7–41).

When Tyr or D-Tyr is added to the extended N-terminus, the peptide can be conveniently radiolabelled using $^{125}$I, or can be otherwise labelled as well known in this art.

In still another aspect, the invention provides CRF agonists having the following formula:

(cyclo 30–33)Y$_1$-R$_7$-R$_8$-Asp-R$_{10}$-R$_{11}$-D-Phe-R$_{13}$-R$_{14}$-R$_{15}$-Arg-R$_{17}$-R$_{18}$ -R$_{19}$-R$_{20}$-R$_{21}$-R$_{22}$-R$_{23}$-R$_{24}$-R$_{25}$-R$_{26}$-R$_{27}$-R$_{28}$-R$_{29}$-Glu-R$_{31}$-R$_{32}$-R$_{33}$-R$_{34}$-Arg-R$_{36}$-R$_{37}$-R$_{38}$-R$_{39}$-R$_{40}$-R$_{41}$-NH$_2$ wherein Y$_1$ is an acyl group having up to 15 carbon atoms but preferably up to 7 carbon atoms, e.g. Ac, Fr, Acr, Bz, Nph or Flu; R$_7$ is Ser(Z$_1$), Ala, Agl(Z$_2$) (Z$_3$), or MeAgl(Z$_2$) (Z$_3$); Z$_1$ is H or OCH$_3$; Z$_2$ is H or lower alkyl; Z$_3$ is H or an acyl group having up to 7 carbon atoms; R$_8$ is Leu or Ile; R$_{10}$ is Leu or CML; R$_{11}$ is Thr or Ser; R$_{13}$ is His, Tyr or Glu; R$_{14}$ is CML or Leu; R$_{15}$ is CML or Leu; R$_{17}$ is Glu, CML, Asn or Lys; R$_{18}$ is Val, Nle, CML or Met; R$_{19}$ is CML, Leu or Ile; R$_{20}$ is Glu, D-Glu, Cys or His; R$_{21}$ is Nle, Ile, CML or Met; R$_{22}$ is Ala, D-Ala, Aib, Thr, Asp or Glu; R$_{23}$ is Arg, Cys, Orn or Lys; R$_{24}$ is Ala, Gln, Ile, Asn, CML or Aib; R$_{25}$ is Asp or Glu; R$_{26}$ is Gln, Asn or Lys; R$_{27}$ is CML, Glu, Gln or Leu; R$_{28}$ is Ala, Lys, Arg or Aib; R$_{29}$ is Gln, Aib or Glu; R$_{31}$ is Aib or an L-isomer of a natural α-amino acid other than Cys; R$_{32}$ is His or D-His or Aib or an L-isomer or D-isomer α-amino acid, examples of which are set forth below; R$_{33}$ is Lys or Orn; R$_{34}$ is Asn or Aib; R$_{36}$ is Lys, Orn, Arg, Har, CML or Leu; R$_{37}$ is CML, Leu, Nle or Tyr; R$_{38}$ is Nle, Met, CML or Leu; R$_{39}$ is Glu, Aib or Asp; R$_{40}$ is Ile, CML, Aib, Thr, Glu, Ala, Val, Leu, Nle, Phe, Nva, Gly or Gln; and R$_{41}$ is Ala, Aib, Ile, CML, Gly, Val, Leu, Nle, Phe, Nva or Gln; wherein Ac-Tyr, Ac-D-Tyr or Ac-Ile may be optionally included at the N-terminus instead of Y$_1$; and wherein D-Phe may be substituted by another D-isomer α-amino acid, such as D-Leu, D-Tyr, D-Cpa, D-Trp, D-Nal or D-Pal or by Phe, Leu or Tyr; provided that a second cyclizing bond may exist between R$_{20}$ and R$_{23}$. As an alternative to acylation at the N-terminus, a sulfonamide may be formed, or a sugar or a lipid can be added to modulate duration of action and solubility.

In yet another aspect, the invention provides CRF agonists having the following formula (including nontoxic salts thereof):

(cyclo 30–33)Y$_1$-R$_7$-R$_8$-Asp-Leu-R$_{11}$-D-Phe-His-R$_{14}$-Leu-Arg-Glu-R$_{18}$-Leu-R$_{20}$-Nle-R$_{22}$-R$_{23}$-Ala-R$_{25}$-Gln-Leu-Ala-R$_{29}$-Glu-Ala-R$_{32}$-R$_{33}$-R$_{34}$-Arg-R$_{36}$-R$_{37}$-Nle-R$_{39}$-R$_{40}$-R$_{41}$-NH$_2$ wherein Y$_1$ is an acyl group having not more than 7 carbon atoms; R$_7$ is Ser(Z$_1$), Ala, Agl(Z$_2$) (Z$_3$), or MeAgl(Z$_2$)(Z$_3$); Z$_1$ is H or OCH$_3$; Z$_2$ is H or lower alkyl; Z$_3$ is H or an acyl group having up to 7 carbon atoms; R$_8$ is Leu or Ile; R$_{11}$ is Thr or Ser; R$_{14}$ is Leu or CML; R$_{18}$ is Val, Nle, CML or Met; R$_{20}$ is Glu or D-Glu; R$_{22}$ is Ala or Thr; R$_{23}$ is Arg or Lys; R$_{25}$ is Asp or Glu; R$_{29}$ is Gln or Glu; R$_{32}$ is His, Aib, D-His, D-Arg, D-2Nal, D-Glu, D-Ala or an equivalent other D-amino acid or Ala; R$_{33}$ is Lys or orn; R$_{34}$ is Asn or Aib; R$_{36}$ is Lys or Leu; R$_{37}$ is Leu or CML; R$_{39}$ is Glu or Asp; R$_{40}$ is Ile, CML or Glu; and R$_{41}$ is Ile, Aib or Ala; wherein Phe may be substituted for D-Phe.

In still another aspect, the invention provides CRF agonists having the following formula (including nontoxic salts thereof):

(cyclo 30–33)Y$_1$-Ser-Leu-Asp-Leu-Thr-D-Phe-R$_{13}$-R$_{14}$-Leu-Arg-R$_{17}$-R$_{18}$-R$_{19}$-Glu-Nle-R$_{22}$-R$_{23}$-R$_{24}$-R$_{25}$-Gln-R$_{27}$-R$_{28}$-R$_{29}$-Glu-R$_{31}$-R$_{32}$-R$_{33}$-R$_{34}$-Arg-R$_{36}$-R$_{37}$-Nle-R$_{39}$-R$_{40}$-R$_{41}$-NH$_2$ wherein Y$_1$ is a acyl group having not more than 7 carbon atoms; R$_{13}$ is His or Tyr; R$_{14}$ is Leu or CML; R$_{17}$ is Glu or CML; $R_{18}$ is Val, CML, Nle or Met; $R_{19}$ is Leu or CML; $R_{22}$ is Ala, Aib or Thr; $R_{23}$ is Arg or Lys; $R_{24}$ is Ala or Aib; $R_{25}$ is Asp or Glu; $R_{27}$ is Leu, CML or Glu; $R_{28}$ is Ala or Aib; $R_{29}$ is Gln, Aib or Glu; $R_{31}$ is Ala or Aib; $R_{32}$ is His, Ala, Aib, D-His or a D-isomer or L-isomer α-amino acid; $R_{33}$ is Lys or Orn; $R_{34}$ is Asn or Aib; $R_{36}$ is Lys, CML or Leu; $R_{37}$ is CML or Leu; $R_{39}$ is Glu, Aib or Asp; $R_{40}$ is Ile, Aib, CML or Glu; and $R_{41}$ is Ala, Aib, CML or Ile; and wherein D-Phe may be substituted by Phe, D-Tyr, D-Cpa, D-Nal or D-Pal.

In still one further aspect, the invention provides CRF agonists having the formula (including nontoxic salts thereof):

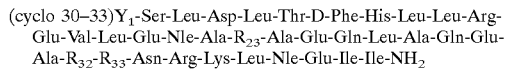
(cyclo 30–33)$Y_1$-Ser-Leu-Asp-Leu-Thr-D-Phe-His-Leu-Leu-Arg-Glu-Val-Leu-Glu-Nle-Ala-$R_{23}$-Ala-Glu-Gln-Leu-Ala-Gln-Glu-Ala-$R_{32}$-$R_{33}$-Asn-Arg-Lys-Leu-Nle-Glu-Ile-Ile-$NH_2$ wherein $Y_1$ is an acyl group having not more than 15 carbon atoms; $R_{23}$ is Arg or Lys; $R_{32}$ is His, D-His, D-Arg, D-Pal, D-Nal or a D-isomer or L-isomer of another natural amino acid other than Cys; $R_{33}$ is Lys or Orn; wherein D-Leu or D-2Nal may be substituted for D-Phe.

In yet one more aspect, the invention provides CRF agonists having the formula (including nontoxic salts thereof):

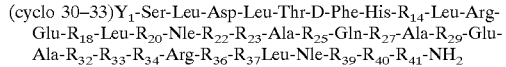
(cyclo 30–33)$Y_1$-Ser-Leu-Asp-Leu-Thr-D-Phe-His-$R_{14}$-Leu-Arg-Glu-$R_{18}$-Leu-$R_{20}$-Nle-$R_{22}$-$R_{23}$-Ala-$R_{25}$-Gln-$R_{27}$-Ala-$R_{29}$-Glu-Ala-$R_{32}$-$R_{33}$-$R_{34}$-Arg-$R_{36}$-$R_{37}$-Leu-Nle-$R_{39}$-$R_{40}$-$R_{41}$-$NH_2$ wherein $R_{14}$ is Leu or CML; $R_{18}$ is Val, Nle, CML or Met; $R_{20}$ is Glu or D-Glu; $R_{22}$ is Ala, Aib or Thr; $R_{23}$ is Arg or Lys; $R_{25}$ is Asp or Glu; $R_{27}$ is Leu or CML; $R_{29}$ is Gln or Glu; $R_{32}$ is His or Ala; $R_{33}$ is Lys or Orn; $R_{34}$ is Asn or Aib; $R_{36}$ is Lys, CML or Leu; $R_{37}$ is CML or Leu; $R_{39}$ is Glu or Asp; $R_{40}$ is Ile, CML or Glu; and $R_{41}$ is Ile, CML, Aib or Ala.

In yet a further aspect, the invention provides CRF agonists having the formula (including nontoxic salts thereof):

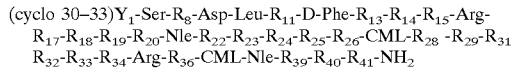
(cyclo 30–33)$Y_1$-Ser-$R_8$-Asp-Leu-$R_{11}$-D-Phe-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-CML-$R_{28}$-$R_{29}$-$R_{31}$-$R_{32}$-$R_{33}$-$R_{34}$-Arg-$R_{36}$-CML-Nle-$R_{39}$-$R_{40}$-$R_{41}$-$NH_2$ wherein $Y_1$ is an acyl group having not more than 7 carbon atoms; wherein $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is D-Glu or Glu; $R_{22}$ is Ala, D-Ala, Aib, Thr, Asp or Glu; $R_{23}$ is Arg or Lys; $R_{24}$ is Ala, CML or Aib; $R_{25}$ is Asp or Glu; $R_{26}$ is Gln, Asn or Lys; $R_{28}$ is Ala or Aib; $R_{29}$ is Gln, Aib or Glu; $R_{31}$ is Ala or Aib; $R_{32}$ is His, D-His, Aib or another L-isomer or D-isomer α-amino acid; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Leu or Phe or Leu may be substituted for D-Phe. Preferably, at least one of $R_{14}$, $R_{18}$, $R_{37}$, and $R_{40}$ is CML in addition to $CML^{27}$. Specific analogs of this group which are considered to be particularly biopotent from the standpoint of reducing blood pressure are:

cyclo(30–33)[Ac-$Ser^7$, D-$Phe^{12}$, $CML^{18,27}$, $Nle^{21,38}$, $Glu^{30}$, $Lys^{33}$]r/hCRF(7–41);

cyclo(30–33)[Ac-$Ser^7$, D-$Phe^{12}$, $CML^{14,27}$, $Nle^{21,38}$, $Glu^{30}$, D-$His^{32}$, $Lys^{33}$]r/hCRF(7–41);

cyclo(30–33)[Ac-$Ser^7$, D-$Phe^{12}$, $CML^{14,27}$, $Nle^{21,38}$, $Glu^{30}$, $Aib^{32}$, $Lys^{33}$]r/hCRF(7–41);

cyclo(30–33)[Ac-$Ser^7$, D-$Phe^{12}$, $Nle^{21,38}$, $CML^{27,37}$, $Glu^{30}$, $Aib^{32}$, $Lys^{33}$]r/hCRF(7–41);

cyclo(30–33)[Ac-$Ser^7$, D-$Phe^{12}$, $Nle^{21,38}$, $CML^{27,40}$, $Glu^{30}$, D-$His^{32}$, $Lys^{33}$]r/hCRF(7–41);

cyclo(30–33)[Ac-$Ser^7$, D-$Phe^{12}$, $Nle^{21,38}$, $CML^{27,40}$, $Glu^{30}$, $Lys^{33}$]r/hCRF(7–41); and cyclo(30–33)[Ac-$Ser^7$, D-$Phe^{12}$, $Nle^{21,38}$, $CML^{27,40}$, $Glu^{30}$, $Aib^{32}$, $Lys^{33}$]r/hCRF(7–41).

In yet another aspect, the invention provides CRF agonists having the formula (including nontoxic salts thereof):

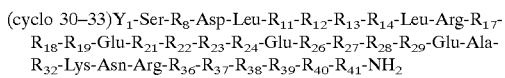
(cyclo 30–33)$Y_1$-Ser-$R_8$-Asp-Leu-$R_{11}$-$R_{12}$-$R_{13}$-$R_{14}$-Leu-Arg-$R_{17}$-$R_{18}$-$R_{19}$-Glu-$R_{21}$-$R_{22}$-$R_{23}$-$R_{24}$-Glu-$R_{26}$-$R_{27}$-$R_{28}$-$R_{29}$-Glu-Ala-$R_{32}$-Lys-Asn-Arg-$R_{36}$-$R_{37}$-$R_{38}$-$R_{39}$-$R_{40}$-$R_{41}$-$NH_2$ wherein $Y_1$ is an acyl group having not more than 7 carbon atoms; $R_8$ is Leu or Ile; $R_{11}$ is Thr or Ser; $R_{12}$ is D-Phe or D-Leu; $R_{13}$ is His or Glu; $R_{14}$ is Leu or CML; $R_{17}$ is Glu, Lys or Asn; $R_{18}$ is Val, CML or Nle; $R_{19}$ is Leu or Ile; $R_{21}$ is Nle or Ile; $R_{22}$ is Ala or Glu; $R_{23}$ is Arg or Lys; $R_{24}$ is Ala, Asn, Gln or Ile; $R_{26}$ is Gln, Asn or Lys; $R_{27}$ is Leu, CML, Glu or Gln; $R_{28}$ is Ala, Arg or Lys; $R_{29}$ is Gln or Glu; $R_{32}$ is His, Gly, Aib, Ala, D-Ala, D-His or another aromatic D-isomer α-amino acid; $R_{36}$ is Lys, Arg, CML or Leu; $R_{37}$ is Leu, CML or Tyr; $R_{38}$ is Nle or Leu; $R_{39}$ is Glu or Asp; $R_{40}$ is Ile, Thr, CML or Glu; and $R_{41}$ is Ala, Ile, CML or Val.

In still another aspect, the invention provides CRF agonists having the formula (including nontoxic salts thereof):

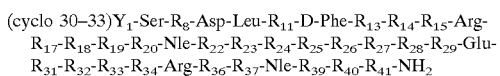
(cyclo 30–33)$Y_1$-Ser-$R_8$-Asp-Leu-$R_{11}$-D-Phe-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-Glu-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein $Y_1$ is an acyl group having not more than 7 carbon atoms; wherein $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is D-Glu or Glu; $R_{22}$ is Ala, D-Ala, Aib, Thr, Asp or Glu; $R_{23}$ is Arg or Lys; $R_{24}$ is Ala or Aib; $R_{25}$ is Asp or Glu; $R_{26}$ is Gln, Asn or Lys; $R_{27}$ is Leu or CML; $R_{28}$ is Ala or Aib; $R_{29}$ is Gln, Aib or Glu; $R_{31}$ is Ala or Aib; $R_{32}$ is His, D-His, Aib, D-Arg, D-2Nal, D-3Pal, Gly, Tyr, D-Tyr, Ala, D-Ala or another aromatic D-isomer α-amino acid; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Leu or Phe or Leu may be substituted for D-Phe.

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following amino acid sequence:

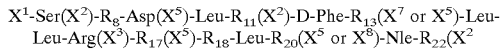

or

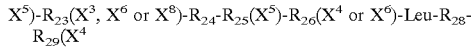

or

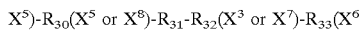

or

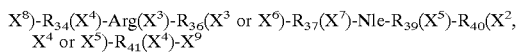

wherein: the R-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl(Fr), acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (Fmoc), cyclopentyloxy-carbonyl, adamantyloxycarbonyl, and cyclohexyloxy-carbonyl; and (5) thiourethan-type protecting groups, such as phenylthiocarbonyl. The two preferred alpha-amino protecting groups are BOC and Fmoc.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl (Xan), for the amido group of Asn or Gln. Asn or Gln is often coupled without side chain protection in the presence of hydroxybenzotriazole (HOBt).

$X^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

$X^6$ is hydrogen or a protecting group for the side chain amino substituent of Lys or Orn. Illustrative of suitable side chain amino-protecting groups are Z, 2-chlorobenzyloxycarbonyl(2Cl-Z), Tos, t-amyloxycarbonyl(Aoc), BOC and aromatic or aliphatic urethan-type protecting groups as specified hereinbefore. 2Cl-Z is preferred for a BOC strategy.

When His is present, $X^7$ is hydrogen or a protecting group for the imidazole nitrogen such as Tos or 2,4-dinitrophenyl (DNP), and when Tyr is present, $X^7$ is hydrogen or a protecting group for the hydroxyl group such as DCB. When Met is present, the sulfur may be protected, if desired, with oxygen.

$X^8$ is a protecting group for the sulfhydryl group of Cys, preferably p-methoxybenzyl(MeOBzl), p-methylbenzyl, acetamidomethyl, trityl or Bzl; or a suitable protecting group for an amino side chain which is removable without simultaneously removing the protecting group $X^6$, e.g. a base-labile group such as Fmoc; or a suitable labile protecting group for a carboxyl side chain which is removable without simultaneously removing the protecting group $X^5$, e.g., a base-labile group such as OFm (fluorenylmethyl ester).

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ is $NH_2$, a protecting group such as an ester or an anchoring bond used in solid phase synthesis for linking to a solid resin support, preferably one of the following: —NH-benzhydrylamine (BHA) resin support and —NH-paramethylbenzhydrylamine (MBHA) resin support. Cleavage from a BHA or MBHA resin directly gives the CRF analog amide. By employing a methyl-derivative of such a resin, a methyl-substituted amide can be created, which is considered to be the equivalent thereof.

In the amino acid sequence for the intermediate, at least one of $X^1$, $X^2$, $X^3$, $X^4$, $X^5$, $X^6$, $X^7$ and $X^8$ is a protecting group or $X^9$ includes resin support. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

If the N-terminus is modified, an acyl group is preferably present, as represented by $Y_1$, and acetyl(Ac), formyl(Fr), acrylyl(Acr) and benzoyl(Bz) are the preferred acyl groups with Nph and Flu being alternatives. Should it be desired to label the peptide, an acylating agent containing a hydroxy aryl moiety, such as 4-hydroxyphenylpropionic acid ($desNH_2$-Tyr) or 4-hydroxy phenylacetic acid, may be used. $Y_1$ may also alternatively be a suitable sugar or lipid, which are generally considered to be equivalents that may be used to adjust hydrophilicity.

Thus, in yet another aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$, $X^7$ and $X^8$ are each either hydrogen or a protective group, and $X^9$ is either a protective group or an anchoring bond to resin support or $NH_2$, (b) forming a cyclizing bond, particularly if one has not already been formed, (c) splitting off the protective group or groups or the anchoring bond from said peptide intermediate, (d) optionally forming a cyclizing bond at this time, and (e) if desired, converting a resulting peptide into a nontoxic addition salt thereof.

The peptides of the invention may be synthesized by classical peptide solution synthesis, and such synthesis is preferred for large quantities. To obtain limited quantities, e.g. less than 1 kg, it may be preferable to prepare them using solid phase synthesis, such as that described by Merrifield, *J. Am. Chem. Soc.*, 85, p. 2149 (1964), which facilitates the CRF agonist peptides being prepared in a straightforward manner and then quickly tested to determine biological activity. This facilitates the ready preparation and evaluation of CRF agonist peptides.

The cyclizing step for the CRF peptide analog depends, of course, upon the precise type of linkage which is desired between the residues in the 30- and 33-positions. To effect an amide cyclizing linkage (lactam bridge), cyclization may be carried out while the partially protected peptide remains attached to the resin as disclosed in U.S. Pat. Nos. 5,064,939 and 5,043,322. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 30-position residue and a side-chain amino group of the 33-position residue, or vice-versa which is generally considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using strategy wherein a base-labile protecting group, e.g., OFm, is initially attached to the carboxyl side-chain of the residue to be involved in the amide-bond bridge and Fmoc is attached to the amino side chain on the other residue that is to be involved. The $\alpha$-amino protecting group on the 1-position residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. If 2 lactam bridges are to be incorporated in the molecule, the 30–33 bridge is preferably effected at a point in the synthesis prior to adding the 23-position residue, or a synthesis protocol such as taught in U.S. Pat. No. 5,064,939 is employed. Following cyclization, the peptide is completely deprotected and cleaved from the resin using a reagent, such as HF. Optionally, a BOC-protecting group may be first removed from the N-terminus using TFA and acylation may optionally be carried out.

A straightforward assay can be carried out using rat anterior pituitary cells in monolayer culture to determine what CRF-activity a candidate peptide will exhibit; the procedure which is used is that generally set forth in *Endocrinology*, 91, 562 (1972). The assay is employed to show whether a candidate peptide will exhibit some activity as a CRF agonist by stimulating ACTH secretion by activating CRF receptors on such cells, and its antagonistic properties are determined by comparison to the results obtained from a parallel dose of oCRF which is used as a laboratory "standard" for this purpose.

A candidate CRF agonist peptide is also easily evaluated in a binding assay using a known CRF receptor, such as that described in Perrin, M., et al., *Endocrinology* 118, 1171–1179 (1986). A representative binding assay utilizing CRF-RA receptor is described in Chen, et al., *P.N.A.S.*, 90, 8967–8971 (October 1993). These cyclic peptides, particularly those having a D-amino acid residue in position 32 exhibit high binding affinity to CRF receptors, such as CRF-RA. As such, they may be used to screen for potential CRF agonists with even higher affinity by using a labelled cyclic CRF agonist.

As hereinbefore indicated, it has been found that the N-terminal acylation of such a CRF family analog which has been N-terminally shortened by the deletion of a sequence of 6 residues, in combination with the 30–33 lactam bridge, creates particularly biopotent CRF agonists which may include the substitution of a D-isomer amino acid in the 32-position. The following examples set forth preferred methods for synthesizing CRF agonists by the solid-phase technique.

EXAMPLE 1

The synthesis of (cyclo 30–33)[Ac-Ser$^7$, D-Phe$^{12}$, Nle$^{21,}$ 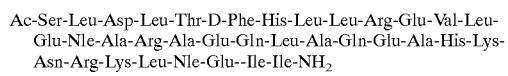 $^{38}$, Glu$^{30}$, Lys$^{33}$]-r/hCRF(7–41) having the amino acid sequence:

Ac-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Glu-Ala-His-Lys-Asn-Arg-Lys-Leu-Nle-Glu-Ile-Ile-NH$_2$ is conducted in a stepwise manner on about 3 grams of a MBHA hydrcochloride resin, such as available from Bachem, Inc., having a substitution range of about 0.1 to 0.5 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | CH$_2$Cl$_2$ wash-80 ml. (2 times) | 1 |
| 2 | Methanol(MeOH) wash-30 ml. (2 times) | 1 |
| 3 | CH$_2$Cl$_2$ wash-80 ml. (3 times) | 1 |
| 4 | 50 percent TFA plus 5 percent 1,2-ethane-dithiol in CH$_2$Cl$_2$-70 ml. (2 times) | 12 |
| 5 | Isopropanol wash-80 ml. (2 times) | 1 |
| 6 | TEA 12.5 percent in CH$_2$Cl$_2$-70 ml. (2 times) | 1 |
| 7 | MeOH wash-40 ml. (2 times) | 1 |
| 8 | CH$_2$Cl$_2$ wash-80 ml. (3 times) | 1 |
| 9 | BOC-amino acid (3–5 molar excess in 30 ml. of either DMF or CH$_2$Cl$_2$, depending upon the solubility of the particular protected amino acid, (1 time) plus DCC (3–5 molar excess)in CH$_2$Cl$_2$ | 30–300 |

Coupling of BOC-Ile results in the substitution of about 0.35 mmol. Ile per gram of resin.

After deprotection and neutralization, the peptide chain is built step-by-step on the resin. Generally, one to two mmol. of BOC-protected amino acid in methylene chloride is used per gram of resin (e.g. a 2–5 fold excess depending on substitution of the resin), plus one equivalent of 2 molar DCC in methylene chloride, for two hours. When BOC-Arg (Tos) is being coupled, a mixture of 50% DMF and methylene chloride is used. Bzl is used as the hydroxyl side-chain protecting group for Ser and Thr. P-nitrophenyl ester(ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain unless the Lys residue is to take part in the lactam bridge when Fmoc is used. Tos is used to protect the guanidino group of Arg and the imidazole group of His, and the side-chain carboxyl group of Glu or Asp is protected by OBzl except for Glu$^{30}$ which is protected by OFm. At the end of the synthesis, the following composition is obtained:

BOC-Ser(Bzl)-Leu-Asp(OBzl)-Leu-Thr(Bzl)-D-Phe-His(Tos)-Leu-
Leu-Arg-(Tos)-Glu(OBzl)-Val-Leu-Glu(OBzl)-Nle-Ala-Arg-
(Tos)-Ala-Glu(OBzl)-Gln(Xan)-Leu-Ala-Gln(Xan)-Glu(OFm)-
Ala-His(Tos)-Lys(Fmoc)-Asn(Xan)-Arg(Tos)-Lys(2Cl-z)-Leu-
Nle-Glu(OBzl)-Ile-Ile-resin support.

Xan may have been partially or totally removed by TFA treatment used to deblock the alpha-amino protecting group.

Next cyclization (lactamization) of residues 30 and 33 is performed by the method referred to hereinbefore and described more fully as follows. After washes with dichloromethane(DCM) (2×) and dimethylformamide (DMF) (2×), the OFm/Fmoc groups of $Glu^{30}$ and $Lys^{33}$, respectively, are removed by 20% piperidine in DMF (1×1 min. and 2×10 min.), followed by washing with DMF (2×), $ET_3N$ in $CH_2Cl_2$ (1×), methanol (MeOH) (2×) and DCM (2×). The peptide-resin is cyclized using a suitable coupling agent, e.g. by reaction at room temperature with threefold excess of benzotriazol-1-yl-oxy-tris(dimethylamino) phosphonium hexafluorophosphate (BOP) in presence of excess diisoproplyethylamine (DIEA) in dimethylformamide (DMF) for four hours. Other suitable reagents are well known and may also be used. After washing, the cyclization may be repeated if desired to assure completion. The completion of the reaction is confirmed by the well known Kaiser ninhydrin test.

Following cyclization, the peptide-resin is treated with TFA to remove the BOC protecting group at the N-terminus. It is then reacted with acetic anhydride to acetylate the proline residue. The resulting peptide-resin is cleaved and deprotected by treatment with 1.5 ml. anisole, 0.5 ml. of methylethylsulfide and 15 ml. hydrogen fluoride (HF) per gram of peptide-resin, first at −20° C. for 20 min. and then at 0° C. for one-half hour. After elimination of the HF under high vacuum, the resin-peptide is washed alternately with dry diethyl ether and chloroform, and the peptide is then extracted with de-gassed 2N aqueous acetic acid and separated from the resin by filtration.

The peptide is purified by gel permeation followed by preparative HPLC as described in Marki, et al., *J. Am. Chem. Soc.*, 103, 3178 (1981); Rivier, et al., *J Chromatography*, 288, 303–328 (1984); and Hoeger, et al., *BioChromatography*, 2, 3, 134–142 (1987). The chromatographic fractions are carefully monitored by HPLC, and only the fractions showing substantial purity are pooled.

To check whether the precise sequence is achieved, the r/hCRF analog is hydrolyzed in sealed evacuated tubes containing constant boiling HCl, 3 μl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 35-residue peptide structure has been obtained.

The peptide is judged to be homogeneous using reversed-phase high performance liquid chromatography (RP-HPLC). It is specifically subjected to RP-HPLC using a Waters HPLC system with a 0.46×25 cm. column packed with 5 μm $C_{18}$ silica, 300 Å pore size and TEAP buffers at different pHs. Desalting of the purified peptide is achieved using Buffer A which is an aqueous 0.1% trifluoroacetic acid solution consisting of 1.0 ml. of TFA per 1000 ml. of solution and Buffer B which is 100% acetonitrile. It has a purity of about 98% measured by capillary zone electrophoresis (CZE). Liquid secondary ion mass spectrometry (LSIMS) mass spectra are measured with a JEOL model JMS-HX110 double-focusing mass spectrometer fitted with a $Cs^+$ gun. An accelerating voltage of 10 kV and $Cs^+$ gun voltage between 25 and 30 kV are employed. The measured value of 4133.44 obtained using LSIMS is in agreement with the calculated value of 4133.34.

The synthesis is repeated twice. Once to create the cyclic peptide with D-His instead of His in the 32-position, and then, by omitting the cyclization step, to produce a comparable linear peptide with $His^{32}$.

The cyclic CRF agonists are examined for their effects on the secretion of ACTH and β-endorphin in vitro and also in vivo. In vitro potency to stimulate the secretion of ACTH and β-endorphin by cultured rat pituitary cells is measured using the procedure generally set forth in *Endocrinology*, 91, 562 (1972) and compared either against synthetic oCRF, the laboratory Standard, or against r/hCRF (an alternate standard). In vivo testing is carried out using the general procedure set forth in C. Rivier et al., *Science*, 218, 377 (1982). In vitro testing of the cyclic $His^{32}$ peptide shows a potency 5.52 times (1.44–21.69) that of the Standard (oCRF), whereas the linear peptide has only about 1% of the potency of the Standard. The D-$His^{32}$ analog is about the same as the cyclic $His^{32}$ analog. The cyclic peptides show a significant lowering of blood pressure when administered peripherally.

Comparative Example A

The synthesis of Example 1 is repeated without acetylating the N-terminus to produce the following peptide: (cyclo 30–33)[D-$Phe^{12}$, $Nle^{21,38}$, $Glu^{30}$, $Lys^{33}$]-r/hCRF(7–41), having the amino acid sequence:

(cyclo 30–33)H-Ser-Leu-Asp-Leu-Thr-D-Phe-His-Leu-Leu-Arg-
Glu-Val-Leu-Glu-Nle-Ala-Arg-Ala-Glu-Gln-Leu-Ala-Gln-Glu-
Ala-His-Lys-Asn-Arg-Lys-Leu-Nle-Glu-Ile-Ile-$NH_2$.

The cyclic peptide has a value of 4091.36 when measured by LSIMS which is in agreement with the calculated value of 4091.32. In vitro testing shows a potency of only 1.35 (0.74–2.59) times the standard in stimulating the secretion of ACTH and β-END-LI, whereas the acetylated version of the same peptide analog shows over 5.5 times the potency of the rCRF standard.

Example 1A

The synthesis of (cyclo 30–33) [Ac-$Ile^6$, D-$Phe^{12}$, $Nle^{21,38}$, $Glu^{30}$, $Lys^{33}$]-r/hCRF(6–41) having the amino acid sequence:

(cyclo 30–33)Ac-Ile-Ser-Leu-Asp-Leu-Thr-D-Phe-His-Leu-Leu-
Arg-Glu-Val-Leu-Glu-Nle-Ala-Arg-Ala-Glu-Gln-Leu-Ala-Gln-
Glu-Ala-His-Lys-Asn-Arg-Lys-Leu-Nle-Glu-Ile-Ile-$NH_2$ is conducted as described in Example 1 above, except that the N-terminus is extended by 1 residue. The peptide has a purity of about 98% measured by CZE, and the LSIMS value of 4246.44 agrees with the calculated value of 4246.42. In vitro testing of the peptide shows a potency of about 7.24 times (1.93–24.32) of that native rCRF standard in stimulating the secretion of ACTH and β-END-LI.

Example 1B

The synthesis of (cyclo 30–33) [Ac-$Ser^7$, D-$Phe^{12}$, $Nle^{21,38}$, $Glu^{30}$, D-$His^{32}$, $Orn^{33}$]-r/hCRF(7–41) having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-Leu-Ala-Gln-Glu-
Ala-D-His-Orn-Asn-Arg-Lys-Leu-Nle-Glu-Ile-Ile-$NH_2$ is conducted as described in Example 1 above, except that residue-33 is Orn instead of Lys. Administration of the peptide stimulates the secretion of ACTH and β-END-LI.

Example 1C

The synthesis of Example 1B is repeated, adding Ac-D-Tyr instead of just acetyl at the N-terminus, to produce the following peptide: (cyclo 30–33)[Ac-D-Tyr$^6$, D-Phe$^{12}$, Nle$^{21,38}$, Glu$^{30}$, Aib$^{32}$, Orn$^{33}$]-r/hCRF(6–41), having the amino acid sequence:

(cyclo 30–33)Ac-D-Tyr-Ser-Leu-Asp-Leu-Thr-D-Phe-His-Leu-Leu-Arg-Glu-Val-Leu-Glu-Nle-Ala-Arg-Ala-Glu-Gln-Lelu-Ala-Gln-Glu-Ala-Aib-Orn-Asn-Arg-Lys-Leu-Nle-Glu-Ile-Ile-NH$_2$.

Administration of the peptide stimulates the secretion of ACTH and β-END-LI. A portion of the peptide is then iodinated with $^{125}$I to provide a ligand for use in competitive drug screening assays.

Example 2

The synthesis of Example 1 is repeated again substituting Ala for His in the 32-position to produce the following peptide: (cyclo 30–33)[Ac-Ser$^7$, D-Phe$^{12}$, Nle$^{21,38}$, Glu$^{30}$, Ala$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Glu-Ala-Ala-Lys-Asn-Arg-Lys-Leu-Nle-Glu-Ile-Ile-NH$_2$.

A portion of the peptide-resin is removed prior to cyclization in order to produce the linear peptide with Ala in the 32-position.

Administration of the cyclic peptide stimulates the secretion of ACTH and β-END-LI. In vitro testing shows that the comparable linear peptide, also having the Ala$^{32}$ substitution, has an in vitro biopotency as an agonist substantially less than the cyclic compound.

Example 3

The peptide (cyclo 30–33)[Ac-Ser$^7$, D-Phe$^{12}$, Nle$^{21,38}$, Glu$^{30}$, D-His$^{32}$, Lys$^{33}$]-oCRF(7–41) having the amino acid sequence:

Ac-Ser-Leu-Asp-Leu-Thr-D-Phe-His-Leu-Leu-Arg-Glu-Val-Leu-Glu-Nle-Thr-Lys-Ala-Asp-Gln-Leu-Ala-Gln-Glu-Ala-D-His-Lys-Asn-Arg-Lys-Leu-Nle-Asp-Ile-Ala-NH$_2$ is synthesized using a procedure generally as set forth in Example 1. A portion of the peptide-resin is removed prior to cyclization, and it is cleaved and deprotected to provide the corresponding linear peptide. The cyclic peptide strongly stimulates the secretion of ACTH and β-END-LI and causes a very significant lowering of blood pressure when administered peripherally. The linear peptide has very significantly lesser bioactivity.

Example 3A

The peptide (cyclo 30–33)[Ac-Ser$^7$, D-Phe$^{12}$, Nle$^{18,21}$, Glu$^{30}$, D-Ala$^{32}$, Lys$^{33}$]-AHC(7–41) having the amino acid sequence:

Ac-Ser-Leu-Asp-Leu-Thr-D-Phe-His-Leu-Leu-Arg-Glu-Nle-Leu-Glu-Nle-Ala-Lys-Ala-Glu-Gln-Glu-Ala-Glu-Glu-Ala-D-Ala-Lys-Asn-Arg-Leu-Leu-Leu-Glu-Glu-Ala-NH$_2$ is synthesized using a procedure generally as set forth in Example 1. A portion of the peptide-resin is removed prior to cyclization, and it is cleaved and deprotected to provide the corresponding linear peptide. The cyclic peptide strongly stimulates the secretion of ACTH and β-END-LI and causes a very significant lowering of blood pressure when administered peripherally. The linear peptide has very significantly lesser bioactivity.

The above synthesis is repeated twice to produce the cyclic peptides with D-His and with Ala in the 32-position. The D-His$^{32}$ and Ala$^{32}$ cyclic analogs also exhibit biopotency greater than the Standard peptide.

Example 3B

The peptide (cyclo 30–33)[Ac-Ser$^7$, D-Phe$^{12}$, Nle$^{18,21}$, Glu$^{30}$, Lys$^{33}$]-sucker urotensin(7–41) having the amino acid sequence:

Ac-Ser-Ile-Asp-Leu-Thr-D-Phe-His-Leu-Leu-Arg-Asn-Nle-Ile-Glu-Nle-Ala-Arg-Ile-Glu-Asn-Glu-Arg-Glu-Glu-Ala-Gly-Lys-Asn-Arg-Lys-Tyr-Leu-Asp-Glu-Val-NH$_2$ is synthesized using a procedure generally as set forth in Example 1.

The synthesis is repeated twice to produce the cyclic peptides with D-Ala and D-His in the 32-position, respectively.

All three cyclic peptides stimulate the secretion of ACTH and β-END-LI and cause a very significant lowering of blood pressure when administered peripherally.

Example 3C

The peptide (cyclo 29–32)[Ac-Ser$^6$, D-Leu$^{11}$, Nle$^{17}$, Glu$^{29}$, Lys$^{32}$]-sauvagine(6–40) having the amino acid sequence:

Ac-Ser-Ile-Asp-Leu-Ser-D-Leu-Glu-Leu-Leu-Arg-Lys-Nle-Ile-Glu-Ile-Glu-Lys-Gln-Glu-Lya-Glu-Lys-Gln-Glu-Ala-Ala-Lys-Asn-Arg-Leu-Leu-Leu-Asp-Thr-Ile-NH$_2$ is synthesized using a procedure generally as set forth in Example 1. A portion of the peptide-resin is removed prior to cyclization, and it is cleaved and deprotected to provide the corresponding linear peptide.

The cyclic peptide stimulates the secretion of ACTH and β-END-LI and causes a very significant lowering of blood pressure when administered peripherally. The linear peptide is significantly less biopotent as an agonist.

The synthesis is repeated to produce the cyclic peptide with D-Ala in the 31-position. The cyclic peptide having the D-Ala$^{31}$ substitution shows biopotency.

Example 3D

The peptide (cyclo 30–33)[Ac-Ser$^7$, D-Phe$^{12}$, Nle$^{21,37,38}$, Glu$^{30}$, Lys$^{33}$]-fish CRF(7–41) having the amino acid sequence:

Ac-Ser-Leu-Asp-Leu-Thr-D-Phe-His-Leu-Leu-Arg-Glu-Val-Leu-Glu-Nle-Ala-Arg-Ala-Glu-Gln-Leu-Ala-Gln-Glu-Ala-His-Lys-Asn-Arg-Lys-Nle-Nle-Glu-Ile-Phe-NH$_2$ is synthesized using a procedure generally as set forth in Example 1. The synthesis is repeated to produce the cyclic peptide with D-His in the 32-position. Both peptides stimulate the secretion of ACTH and β-END-LI and cause a very significant lowering of blood pressure when administered peripherally.

Example 3E

The peptide (cyclo 30–33)[Ac-Ser$^7$, D-Phe$^{12}$, Nle$^{14,18,24}$, Glu$^{30}$, D-Leu$^{32}$, Lys$^{33}$]-maggy urotensin(7–41) having the amino acid sequence:

Ac-Ser-Ile-Asp-Leu-Thr-D-Phe-His-Nle-Leu-Arg-Asn-Nle-Ile-His-Arg-Ala-Lys-Nle-Glu-Gly-Glu-Arg-Glu-Glu-Ala-D-Leu-Lys-Asn-Arg-Asn-Leu-Leu-Asp-Glu-Val-NH$_2$ is synthesized using a procedure generally as set forth in Example 1. The synthesis is repeated to produce the cyclic peptide with D-His in the 32-position. Both peptides stimulate the secretion of ACTH and β-END-LI and cause a very significant lowering of blood pressure when administered peripherally.

Example 3F

The peptide (cyclo 30–33)[Ac-Ser$^7$, D-Phe$^{12}$, Nle$^{18,21}$, Glu$^{30}$, D-Ala$^{32}$, Lys$^{33}$]-carp urotensin(7–41) having the amino acid sequence:

Ac-Ser-Ile-Asp-Leu-Thr-D-Phe-His-Leu-Leu-Arg-Asn-Nle-Ile-Glu-
Nle-Ala-Arg-Asn-Glu-Asn-Gln-Arg-Glu-Glu-Ala-D-Ala-Lys-
Asn-Arg-Lys-Tyr-Leu-Asp-Glu-Val-NH$_2$ is synthesized using a procedure generally as set forth in Example 1. The synthesis is repeated to produce the comparable cyclic peptide with D-His in the 32-position. Both peptides stimulate the secretion of ACTH and β-END-LI and cause a very significant lowering of blood pressure when administered peripherally.

Example 3G

The peptide (cyclo 30–33)[Ac-Ser$^7$, D-Phe$^{12}$, Nle$^{14,18,24}$, Glu$^{30}$, D-Gln$^{32}$, Lys$^{33}$]-flounder urotensin(7–41) having the amino acid sequence:

Ac-Ser-Ile-Asp-Leu-Thr-D-Phe-His-Nle-Leu-Arg-Asn-Nle-Ile-is-
Arg-Ala-Lys-Nle-Glu-Gly-Glu-Arg-Glu-Glu-Ala-D-Gln-Lys-
Asn-Arg-Asn-Leu-Leu-Asp-Glu-Val-NH$_2$ is synthesized using a procedure generally as set forth in Example 1. The synthesis is repeated to produce the cyclic peptide with D-His in the 32-position. Both peptides stimulate the secretion of ACTH and β-END-LI and cause a very significant lowering of blood pressure when administered peripherally.

Example 3H

The peptide (cyclo 30–33)[Ac-Ser$^7$, D-Phe$^{12}$, Nle$^{21,38}$, Glu$^{30}$, Lys$^{33}$]-porcine CRF(7–41) having the amino acid sequence:

Ac-Ser-Leu-Asp-Leu-Thr-D-Phe-His-Leu-Leu-Arg-Glu-Val-Leu-
Glu-Nle-Ala-Arg-Ala-Glu-Gln-Leu-Ala-Gln-Glu-Ala-His-Lys-
Asn-Arg-Lys-Leu-Nle-Glu--Asn-Phe-NH$_2$ is synthesized using a procedure generally as set forth in Example 1. The synthesis is repeated to produce the cyclic peptide with D-His in the 32-position. Both peptides stimulate the secretion of ACTH and β-END-LI and cause a very significant lowering of blood pressure when administered peripherally.

Example 4

The synthesis of (bicyclo 20–23, 30–33) [Ac-Ser$^7$, D-Phe$^{12}$, Nle$^{21,38}$, Lys$^{23,33}$, Glu$^{30}$, D-His$^{32}$]-r/hCRF(7–41) having the amino acid sequence:

(bicyclo 20–23, 30–33)Ac-Ser-Leu-Asp-Leu-Thr-D-Phe-His-Leu-
Leu-Arg-Glu-Val-Leu-Glu-Nle-Ala-Lys-Ala-Glu-Gln-Leu-Ala-
Gln-Glu-Ala-D-His-Lys-Asn-Arg-Lys-Leu-Nle-Glu-Ile-Ile-NH$_2$ is conducted as generally described in Example I above, except that the lactam bridge between residues 30 and 33 is completed before residue 23 is added to the peptide-resin. Administration of the peptide stimulates the secretion of ACTH and β-END-LI, and iv injection lowers blood pressure.

Example 5

A synthesis as in Example 1 is performed substituting D-Glu for Glu in the 20-position to produce the following peptide: (cyclo 30–33)[Ac-Ser$^7$, D-Phe$^{12}$, D-Glu$^{20}$, Nle$^{21,38}$, Glu$^{30}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-D-Glu-Nle-Ala-Arg-Ala-Glu-Gln-Leu-Ala-Gln-
Glu-Ala-His-Lys-Leu-Nle-Glu-Ile-Ile-NH$_2$.

The cyclic peptide has a value of 4133.38 when measured by LSIMS which is in agreement with the calculated value of 4133.33. In vitio testing of the cyclic peptide for the stimulation of secretion of ACTH and β-END-LI shows a potency of about 5.49 times (3.29–9.43) that of the CRF standard. The comparable linear peptide has a biopotency only about 1% of the Standard.

Example 5A

A synthesis as in Example 1 is performed substituting D-Ser for Ser at the N-terminus to produce the following peptide: (cyclo 30–33)[Ac-D-Ser$^7$, D-Phe$^{12}$, Nle$^{21,38}$, Glu$^{30}$, Lys$^{33}$]-r/hCRF(7–41), having the amino acid sequence:

(cyclo 30–33)Ac-D-Ser-Leu-Asp-Leu-Thr-D-Phe-His-Leu-Leu-
Arg-Glu-Val-Leu-Glu-Nle-Ala-Arg-Ala-Glu-Gln-Leu-Ala-Gln-
Glu-Ala-His-Lys-Asn-Arg-Lys-Leu-Nle-Glu-Ile-Ile-NH$_2$.

The cyclic peptide has a value of 4133.4 when measured by LSIMS which is in agreement with the calculated value of 4133.34. In vitro testing for the stimulation of ACTH secretion shows a potency of 3.08 (1.85–5.17) compared to the Standard. Administration of the cyclic peptide stimulates the secretion of ACTH and β-END-LI.

Example 5B

A synthesis as in Example 1 is performed substituting Ala for Ser at the N-terminus to produce the following peptide: (cyclo 30–33)[Ac-Ala$^7$, D-Phe$^{12}$, Nle21,38, Glu$^{30}$, Lys$^{33}$]-r/hCRF(7–41), having the amino acid sequence:

(cyclo 30–33)Ac-Ala-Leu-Asp-Leu-Thr-D-Phe-His-Leu-Leu-Arg-
Glu-Val-Leu-Glu-Nle-Ala-Arg-Ala-Glu-Gln-Leu-Ala-Gln-Glu-
Ala-His-Lys-Asn-Arg-Lys-Leu-Nle-Glu-Ile-Ile-NH$_2$.

The cyclic peptide has a value of 4117.3 when measured by LSIMS which is in agreement with the calculated value of 4117.34. Administration of the cyclic peptide stimulates the secretion of ACTH and β-END-LI, and in vitro testing shows ACTH secretion of about 4.3 times (2.069–9.516) that of the Standard.

Example 6A

A synthesis as in Example 1 is performed, substituting Aib for His in the 32-position, to produce the following peptide: (cyclo 30–33)[Ac-Ser$^7$, D-Phe$^{12}$, Nle$^{21,38}$, Glu$^{30}$, Aib$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-Leu-Ala-Gln-Glu-
Ala-Aib-Lys-Asn-Arg-Lys-Leu-Nle-Glu-Ile-Ile-NH$_2$.

Administration of the peptide stimulates the secretion of ACTH and β-END-LI, and peripheral administration significantly lowers blood pressure.

Example 6B

A synthesis as in Example 1 is performed, substituting D-Lys for His$^{32}$, to produce the following peptide: (cyclo 30–33)[Ac-Ser$^7$, D-Phe$^{12}$, Nle$^{21,38}$, Glu$^{30}$, D-Lys$^{32}$, Ly$^{33}$-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-Leu-Ala-Gln-Glu-
Ala-D-Lys-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 6C

A synthesis as in Example 1 is performed, substituting D-2Nal for His$^{32}$, to produce the following peptide: (cyclo 30–33)[Ac-Ser$^7$, D-Phe$^{12}$, Nle$^{21,38}$, Glu$^{30}$, D-2Nal$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-Leu-Ala-Gln-Glu-
Ala-D-2Nal-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 7

The synthesis of (bicyclo 20–23, 30–33) [Ac-Ser$^7$, D-Phe$^{12}$, Nle$^{21,38}$, Lys$^{23,33}$, Glu$^{30}$]-r/hCRF(7–41) having the amino acid sequence:

(bicyclo 20–23, 30–33)Ac-Ser-Leu-Asp-Leu-Thr-D-Phe-His-Leu-
Leu-Arg-Glu-Val-Leu-Glu-Nle-Ala-Lys-Ala-Glu-Gln-Leu-Ala-
Gln-Glu-Ala-His-Lys-Asn-Arg-Lys-Leu-Nle-Glu-Ile-Ile-NH$_2$ is conducted as generally described in Example 4 above.

Administration of the peptide stimulates the secretion of ACTH and β-END-LI, and iv injection lowers blood pressure.

Example 8

A synthesis as in Example 1 is carried out substituting C$^\alpha$MeLeu for Leu$^{15}$ to produce the following peptide: (cyclo 30–33)[Ac-Ser$^7$, D-Phe$^{12}$, CML$^{15}$, Nle$^{21,38}$, Glu$^{30}$, D-His$^{32}$, Lys$^{33}$]-r/hCRF(7–41), having the amino acid sequence:

(cyclo 30–33)Ac-Ser-Leu-Asp-Leu-Thr-D-Phe-His-Leu-CML-Arg-
Glu-Val-Leu-Glu-Nle-Ala-Arg-Ala-Glu-Gln-Leu-Ala-Gln-Glu-
Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 8A

A synthesis as in Example 1 is performed substituting C$^\alpha$MeLeu for Leu$^{14}$ to produce the following peptide: (cyclo 30–33)(Ac-Ser$^7$, D-Phe$^{12}$, CML$^{14}$, Nle$^{21,38}$, Glu$^{30}$, D-His$^{32}$, Lys$^{33}$]-r/hCRF(7–41), having the amino acid sequence:

(cyclo 30–33)Ac-Ser-Leu-Asp-Leu-Thr-D-Phe-His-CML-Leu-Arg-
Glu-Val-Leu-Glu-Nle-Ala-Arg-Ala-Glu-Gln-Leu-Ala-Gln-Glu-
Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 8B

A synthesis as in Example 1 is carried out substituting C$^\alpha$MeLeu for Leu$^{19}$ to produce the following peptide: (cyclo 30–33)[Ac-Ser$^7$, CML$^{19}$, Nle$^{21,38}$, Glu$^{30}$, D-His$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-CML-Glu-Nle-Ala-Arg-Ala-Glu-Gln-Leu-Ala-Gln-Glu-
Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 8C

A synthesis as in Example 1 is performed substituting C$^\alpha$MeLeu for Leu$^{27}$ to produce the following peptide: (cyclo 30–33)[Ac-Ser$^7$, D-Phe$^{12}$, Nle$^{21,38}$, CML$^{27}$, Glu$^{30}$, D-His$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 8D

A synthesis as in Example 1 is performed substituting C$^\alpha$MeLeu for Leu$^{37}$ to produce the following peptide: (cyclo 30–33)[Ac-Ser$^7$, D-Phe$^{12}$, Nle$^{21,38}$, Glu$^{30}$, D-His$^{32}$, Lys$^{33}$, CML$^{37}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Aln-Leu-Ala-Gln-Glu-
Ala-D-His-Lys-Asn-Arg-Lys-CML-Nle-Glu-Ile-Ile-NH$_2$.

Administration of the peptide stimulates the secretion of ACTH and β-END-LI, and iv injection lowers blood pressure.

Example 8E

A synthesis as in Example 1 is carried out substituting C$^\alpha$MeLeu for Glu$^{17}$ to produce the following peptide: (cyclo 30–33)[Ac-Ser$^7$, D-Phe$^{12}$, CML$^{17}$, Nle$^{21,38}$, Glu$^{30}$, D-His$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
CML-Val-Leu-Glu-Nle-Ala-Arg-Ala-Glu-Gln-Leu-Ala-Gln-Glu-
Ala-D-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 9A

The synthesis as in Example 1 is performed substituting C$^\alpha$MeLeu for Leu$^{27}$ to produce the following peptide: (cyclo 30–33)[Ac-Ser$^7$, D-Phe$^{12}$, Nle$^{21,38}$, CML$^{27}$, Glu$^{30}$, Lys$^{33}$]-r/hCRF(7–41), having the formula:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 9B

The synthesis of Example 9A is repeated, but this time also substituting C$^\alpha$MeLeu for Leu$^{14}$, to produce the following peptide: (cyclo 30–33)[Ac-Ser$^7$, D-Phe$^{12}$, CML$^{14,27}$, Nle$^{21,38}$, Glu$^{30}$, Lys$^{33}$]-r/hCRF(7–41), having the formula:

(cyclo 30–33)Ac-Ser-Leu-Asp-Leu-Thr-D-Phe-His-CML-Leu-Arg-
Glu-Val-Leu-Glu-Nle-Ala-Arg-Ala-Glu-Gln-CML-Ala-Gln-Glu-
Ala-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 9C

The synthesis of Example 9A is repeated again, but this time also substituting C$^\alpha$MeLeu for Val$^{18}$, to produce the following peptide: (cyclo 30–33)[Ac-Ser$^7$, D-Phe$^{12}$, CML$^{18, 27}$, Nle$^{21,38}$, Glu$^{30}$, Lys$^{33}$]-r/hCRF(7–41), having the formula:

(cyclo 30–33)Ac-Ser-Leu-Asp-Leu-Thr-D-Phe-His-Leu-Leu-Arg-
Glu-CML-Leu-Glu-Nle-Ala-Arg-Ala-Glu-Gln-Leu-Ala-Gln-
Glu-Ala-His-Lys-Asn-Arg-Lys-Leu-Nle-Glu-Ile-Ile-NH$_2$.

Administration of the peptide stimulates the secretion of ACTH and β-END-LI, and iv injection lowers blood pressure.

Example 9D

The synthesis of Example 9A is repeated once more, also substituting C$^\alpha$MeLeu for Lys$^{36}$, to produce the following peptide: (cycle 30–33)[Ac-Ser$^7$, D-Phe$^{12}$, Nle$^{21,38}$, CML$^{27, 36}$, Glu$^{30}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-His-Lys-Asn-Arg-CML-Leu-Nle-Glu-Ile-Ile-NH$_2$.

Administration of the peptide stimulates the secretion of ACTH and β-END-LI, and iv injection lowers blood pressure.

The above synthesis is generally repeated, substituting D-His for His$^{32}$, to produce the following peptide: (cyclo 30–33)[Ac-Ser$^7$, D-Phe$^{12}$, Nle$^{21,38}$, CML$^{27,36}$, Glu$^{30}$, D-His$^{32}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-D-His-Lys-Asn-Arg-CML-Leu-Nle-Glu-Ile-Ile-NH$_2$.

Administration of the peptide stimulates the secretion of ACTH and β-END-LI and iv injection lowers blood pressure.

Example 9E

The synthesis of Example 9A is repeated, substituting C$^\alpha$MeLeu for Leu$^{37}$, to produce the following peptide: (cyclo 30–33)[Ac-Ser$^7$, D-Phe$^{12}$, Nle$^{21,38}$, CML$^{27,37}$, Glu$^{30}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-His-Lys-Asn-Arg-Lys-CML-Nle-Glu-Ile-Ile-NH$_2$.

Administration of the peptide stimulates the secretion of ACTH and β-END-LI, and iv injection lowers blood pressure.

Example 9F

The synthesis of Example 9A is repeated again, but this time also substituting C$^\alpha$MeLeu for Ile$^{40}$, to produce the following peptide: (cyclo 30–33)[Ac-Ser$^7$, D-Phe$^{12}$, Nle$^{21,38}$, CML$^{27,40}$, Glu$^{30}$, Lys$^{33}$]-r/hCRF (7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-His-Lys-Asn-Arg-Lys-Leu-Nle-Glu-CML-Ile-NH$_2$.

The above synthesis is repeated twice, first substituting D-His for His$^{32}$, and then substituting Aib for His$^{32}$ to produce the peptide: (cyclo 30–33)[Ac-Ser$^7$, D-Phe$^{12}$, Nle$^{21, 38}$, CML$^{27,40}$, Glu$^{30}$, Aib$^{32}$, Lys$^{33}$]-r/hCRF(7–41).

Administration of these peptides stimulates the secretion of ACTH and β-END-LI, and iv injection lowers blood pressure.

Example 9G

The synthesis of Example 9A is repeated again, but this time also substituting C$^\alpha$MeLeu for Ile$^{41}$, to produce the following peptide: (cyclo 30–33)[Ac-Ser$^7$, D-Phe$^{12}$, Nle$^{21, 38}$, CML$^{27,41}$, Glu$^{30}$, Lys$^{33}$]-r/hCRF(7–41), having the amino acid sequence:

(cyclo 30–33)Ac-Ser-Leu-Asp-Leu-Thr-D-Phe-His-Leu-Leu-Arg-
Glu-Val-Leu-Glu-Nle-Ala-Arg-Ala-Glu-Gln-CML-Ala-Gln-Glu-
Ala-His-Lys-Asn-Arg-Lys-Leu-Nle-Glu-Ile-CML-NH$_2$.

The above synthesis is repeated, substituting D-His for His$^{32}$, to produce the peptide: (cyclo 30–33)[Ac-Ser$^7$, D-Phe$^{12}$, Nle$^{21,38}$, CML$^{27,41}$, Glu$^{30}$, D-His$^{32}$, Lys$^{33}$]-r/hCRF(7–41).

Administration of these peptides stimulates the secretion of ACTH and β-END-LI, and iv injection lowers blood pressure.

Example 9H

The synthesis of Example 9A is repeated a number of times, each time also making an additional substitution of Aib for a different residue. As a result, the following (30–33) cyclic peptides are produced:

[Ac-Ser$^7$, D-Phe$^{12}$, Nle$^{21,38}$, Aib$^{22}$, CML$^{27}$, Glu$^{30}$, Lys$^{33}$]-r/hCRF (7–41);

[Ac-Ser$^7$, D-Phe$^{12}$, Nle$^{21,38}$, Aib$^{24}$, CML$^{27}$, Glu$^{30}$, Lys$^{33}$]-r/hCRF (7–41);

[Ac-Ser$^7$, D-Phe$^{12}$, Nle$^{21,38}$, CML$^{27}$, Aib$^{28}$, Glu$^{30}$, Lys$^{33}$]-r/hCRF (7–41);

[Ac-Ser$^7$, D-Phe$^{12}$, Nle$^{21,38}$, CML$^{27}$, Aib$^{29}$, Glu$^{30}$, Lys$^{33}$]-r/hCRF (7–41);

[Ac-Ser$^7$, D-Phe$^{12}$, Nle$^{21,38}$, CML$^{27}$, Glu$^{30}$, Aib$^{31}$, Lys$^{33}$]-r/hCRF (7–41);

[Ac-Ser$^7$, D-Phe$^{12}$, Nle$^{21,38}$, CML$^{27}$, Glu$^{30}$, Lys$^{33}$, Aib$^{34}$]-r/hCRF (7–41);

[Ac-Ser$^7$, D-Phe$^{12}$, Nle$^{21,38}$, CML$^{27}$, Glu$^{30}$, Lys$^{33}$, Aib$^{39}$]-r/hCRF (7–41);

[Ac-Ser$^7$, D-Phe$^{12}$, Nle$^{21,38}$, CML$^{27}$, Glu$^{30}$, Lys$^{33}$, Aib$^{40}$]-r/hCRF (7–41);

[Ac-Ser$^7$, D-Phe$^{12}$, Nle$^{21,38}$, CML$^{27}$, Glu$^{30}$, Lys$^{33}$, Aib$^{41}$]-r/hCRF (7–41); and

[Ac-Ser$^7$, D-Phe$^{12}$, Nle$^{21,38}$, CML$^{27}$, Glu$^{30}$, Aib$^{32}$, Lys$^{33}$]-r/hCRF (7–41).

Administration of these peptides stimulates the secretion of ACTH, and iv injection lowers blood pressure.

Example 10

Using the procedure as generally set forth in Example 1, the following CRF agonist peptides are also prepared:

| | |
|---|---|
| (c 30–33) | [Ac-Ser$^7$, Glu$^{30}$, D-His$^{32}$, Lys$^{33}$]-AHC(7–41) |
| " | [Ac-Ser$^7$, CML$^{17}$, Glu$^{30}$, D-Ala$^{32}$, Lys$^{33}$]-oCRF(7–41) |
| " | [Ac-Ile$^6$, CML$^{14}$, D-Glu$^{20}$, Nle$^{21,38}$, Glu$^{30}$, D-Tyr$^{32}$, Lys$^{33}$]-r/hCRF (6–41) |
| " | [Ac-Ser$^7$, D-2Nal$^{12}$, CML$^{14}$, Glu$^{30}$, D-2Nal$^{32}$, Lys$^{33}$]-oCRF(7–41) |
| " | [Ac-Ser$^7$, CML$^{17}$, Nle$^{18,21}$, Glu$^{30}$, D-Arg$^{32}$, Lys$^{33}$]-AHC(7–41) |

-continued

| (c 30–33) | [Ac-Ile$^6$, D-Glu$^{20}$, Glu$^{30}$, D-Leu$^{32}$, Lys$^{33}$]-r/hCRF (6–41) |
| " | [Ac-Ser$^7$, D-Phe$^{12}$, CML$^{17,37}$, Nle$^{21}$, Glu$^{30}$, Tyr$^{32}$, Lys$^{33}$, Aib$^{41}$]-oCRF(7–41) |
| " | [Ac-Ile$^6$, D-4Cpa$^{12}$, Glu$^{30}$, Arg$^{32}$, Lys$^{33}$]-AHC(6–41) |
| " | [Ac-Ile$^6$, D-Tyr$^{12}$, CML$^{15}$, Nle$^{21,38}$, Glu$^{30}$, D-Val$^{32}$, Lys$^{33}$, Aib$^{40}$]-r/hCRF(6–41) |
| " | [Ac-Ser$^7$, D-Glu$^{20}$, Nle$^{21,38}$, Glu$^{30}$, D-Ser$^{32}$, Lys$^{33}$]-r/hCRF (7–41) |
| " | [Ac-Ser$^7$, D-Leu$^{12}$, CML$^{17,37}$, Nle$^{21,38}$, Glu$^{30}$, D-Asn$^{32}$, Lys$^{33}$Aib$^{39}$]-r/hCRF(7–41) |
| " | [Ac-Ile$^6$, Nle$^{18,21}$, Glu$^{30}$, D-4Cpa$^{32}$, Lys$^{33}$, Aib$^{34,40}$]-AHC(6–41) |
| " | [Ac-Ser$^{71}$, CML$^{17}$, D-Glu$^{20}$, Glu$^{30}$, D-3Pal$^{32}$, Lys$^{33}$, Aib$^{34}$]-r/hCRF(7–41) |
| " | [Ac-Ile$^6$, CML$^{17,37}$, Nle$^{21,38}$, Glu$^{30}$, Aib$^{32}$, Lys$^{33}$]-r/hCRF (6–41) |
| " | [Ac-Ser$^7$, D-Phe$^{12}$, CML$^{19}$, Glu$^{30}$, 2Nal$^{32}$, Lys$^{33}$]-r/hCRF(7–41) |
| " | [Ac-Ile$^6$, D-Pal$^{12}$, Nle$^{21}$, Aib$^{22}$, CML$^{27,37}$, Glu$^{30}$, D-Phe$^{32}$, Lys$^{33}$]-oCRF(6–41) |
| " | [Ac-Ser$^7$, D-Glu$^{20}$, CML$^{27}$, Glu$^{30}$, D-Gln$^{32}$, Lys$^{33}$, Aib$^{41}$]-AHC(7–41) |
| " | [Acr-Ser$^7$, D-Phe$^{12}$, Nle$^{21,38}$, Glu$^{30}$, Ala$^{32}$, Lys$^{33}$, Aib$^{39}$]-r/hCRF(7–41) |
| " | [Ac-Ser$^7$, D-Phe$^{12}$, Nle$^{21,38}$, Glu$^{30}$, D-Orn$^{32}$, Lys$^{33}$]-r/hCRF(7–41) |
| " | [Ac-Ile$^6$, D-Phe$^{12}$, Nle$^{21,38}$, Glu$^{30}$, D-Orn(Nic)$^{32}$, Lys$^{33}$]-r/hCRF(6–41) |
| " | [Ac-Ser$^7$, D-Phe$^{12}$, Nle$^{21,38}$, Glu$^{30}$, D-Dbu$^{32}$, Lys$^{33}$, Aib$^{40}$]-r/hCRF (7–41) |
| " | [Ac-Ile$^6$, D-Phe$^{12}$, Nle$^{21,38}$, Glu$^{30}$, D-Lys$^{32}$, Lys$^{33}$]-r/hCRF (6–41) |
| " | [Ac-Ser$^7$, D-Phe$^{12}$, Nle$^{21,38}$, Aib$^{28}$, Glu$^{30}$, D-Aph$^{32}$, Lys$^{33}$]-r/hCRF(7–41) |
| " | [Ac-Ser$^7$, D-Phe$^{12}$, Nle$^{21,38}$, Glu$^{30}$, Aib$^{31}$, D-1Nal$^{32}$, Lys$^{33}$]-r/hCRF (7–41) |
| " | [Nph-Ser$^7$, D-Phe$^{12}$, Nle$^{21,38}$, Glu$^{30}$, D-Dpr$^{32}$, Lys$^{33}$]-r/hCRF(7–41) |
| (c 30–33) | [Ac-Ser$^7$, D-Phe$^{12}$, Nle$^{21,38}$, Aib$^{29}$, Glu$^{30}$, Phe$^{32}$, Lys$^{33}$]-r/hCRF(7–41) |
| " | [Ac-Ile$^6$, D-Phe$^{12}$, Nle$^{21,38}$, Aib$^{22}$, Glu$^{30}$, D-Tyr$^{32}$, Lys$^{33}$]-r/hCRF(6–41) |
| " | [Ac-Ser$^7$, D-Phe$^{12}$, Nle$^{21,38}$, Glu$^{30}$D-Agl(Nic)$^{32}$, Lys$^{33}$]-r/hCRF(7–41) |
| " | [Ac-Ser$^7$, D-Phe$^{12}$, Nle$^{21,38}$, Aib$^{24}$, Glu$^{30}$, D-Aph(methyl)$^{32}$, Lys$^{33}$]-r/hCRF(7–41) |
| " | [Flu-Ser$^7$, D-Phe$^{12}$, Nle$^{21,38}$, Aib$^{28}$, Glu$^{30}$, D-Glu$^{32}$, Lys$^{33}$]-r/hCRF(7–41) |
| " | [Ac-Ser$^7$, D-Phe$^{12}$, Nle$^{21,38}$, Aib$^{24}$, Glu$^{30}$, Asn$^{32}$, Lys$^{33}$, CML$^{37}$]-r/hCRF(7–41) |
| " | [Ac-Ile$^{61}$, D-Phe$^{12}$, Nle$^{21,38}$, Aib$^{22}$, Glu$^{30}$, 3Pal$^{32}$, Lys$^{33}$, CML$^{40}$]-r/hCRF(6–41) |
| " | [Ac-Ser$^7$-D-Phe$^{12}$, Nle$^{21,38}$, Aib$^{24}$, CML$^{27}$, Glu$^{30}$, D-Thr$^{32}$, Lys$^{33}$]-r/hCRF (7–41) |

These peptides are biopotent in stimulating the secretion of ACTH and β-END-LI and in decreasing systemic blood pressure when administered intravenously.

CRF profoundly stimulates the pituitary-adrenalcortical axis, and acts within the brain to mediate a wide range of stress responses. CRF agonists should be useful to stimulate the functions of this axis in some types of patients with low endogenous glucocorticoid production. For example, CRF agonists should be useful in restoring pituitary-adrenal function in patients having received exogenous glucocorticoid therapy whose pituitary-adrenalcortical functions remain suppressed.

CRF agonist peptides of the invention are also therapeutically useful to modulate blood flow in many various vascular beds, and particularly in desired tissues and organs. CRF analogs are of use for increasing blood flow to the gastrointestinal tract of animals, particularly humans and other mammals, as they are shown to dilate the mesenteric vascular bed. CRF has been shown to modulate vascular permeability (Wei E. T. et al., "Peripheral anti-inflammatory actions of corticotropin-releasing factor", pp. 258–276, *Corticotropin-Releasing Factor* (Ciba Foundation Symposium 172) John Wiley & Sons, 1993), and these CRF agonists will also reduce vascular leakage and have a salutary effect on injury- or surgery-induced tissue swelling and inflammation. Therefore, CRF agonists can be administered parenterally to decrease inflammation, swelling and edema and to reduce fluid loss following heat injury.

oCRF, r/hCRF, urotensin I and sauvagine have been shown to inhibit gastric acid production, and the CRF agonists of the invention are considered to also be effective in the treatment of gastric ulcers by reducing gastric acid production and/or inhibiting certain gastrointestinal functions in a mammal. CRF agonists will be effective in increasing intestinal transit rate and useful in the treatment of acute constipation. The CRF agonist peptides of the invention are also considered useful in treating intestinal and gastrointestinal disorders, such as irritable bowel syndrome.

These CRF agonist peptides may also be used to evaluate hypothalamic pituitary adrenal function in mammals with suspected endocrine or central nervous system pathology by suitable administration followed by monitoring bodily functions. For example, administration may be used as a diagnostic tool to evaluate Cushing's disease and affective disorders, such as depressive illness.

CRF agonists or the nontoxic addition salts thereof, combined with a pharmaceutically or veterinarily acceptable carrier, may be administered to mammals, including humans, either intravenously, subcutaneously, intramuscularly, intrapulmonarily, percutaneously, e.g. intranasally, intracerebroventricularly or orally. The peptides should be at least about 90% pure and preferably should have a purity of at least about 98%. The required dosage will vary with the particular condition being treated, with the severity of the condition and with the duration of desired treatment, and multiple dosages may be used for a single day. For parental administration, solutions in peanut oil, in aqueous propylene glycol, or in sterile aqueous solution may be employed. Such aqueous solutions, which are suitably buffered, are especially suitable for intravenous, intramuscular, subcutaneous (s.c.) and intraperitoneal administration. Sterile aqueous media are readily available, and for s.c. administration, corn oil or a 3–6% mannitol solution may be preferred. Such peptides are often administered in the form of pharmaceutically acceptable nontoxic salts, such as acid addition salts or metal complexes. The salts of trifluoroacetic acid and pamoic acid may be preferred.

The peptides should be administered under the guidance of a physician in single or multiple doses, and pharmaceutical compositions will usually contain the peptide in conjunction with a conventional, pharmaceutically-acceptable carrier. The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal per day. For the treatment of certain indications daily dosages up to about 100 mg/kg may be employed. The daily dosage may be given in a single dose or up to three divided doses.

As mentioned hereinbefore, CRF receptors have now been cloned and binding affinity tests and binding assays employing CRF receptors are readily carried out with initially identified or synthesized peptides to determine whether such peptides will likely be effective CRF agonists as described in WO 96/18649. Such receptor assays can be used as screens for potential drugs which interact with CRF and/or CRF receptors.

As used herein all temperatures are ° C. and all ratios are by volume. Percentages of liquid materials are also by volume.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. There are known additional substitutions and modifications at other positions in the CRF peptide chain that can be made without detracting from the potency of the CRF agonists, and developments to this date have shown that a r/hCRF agonist having the 30–33 lactam bond will retain its improved biopotency even if multiple of such substitutions are incorporated. For example, D-Ala$^{31}$ can be substituted for Ala$^{31}$ with retention of biopotency well above that of the native sequence and is thus considered equivalent. Instead of D-Phe in the 12-position, L-Phe or another appropriate D-isomer generally similar to those hereinbefore mentioned, e.g. D-Cpa, may be present, and such are considered to be equivalent, although a D-isomer is preferred. The N-terminus of r/hCRF(7–41) can be extended by Ile, Tyr or D-Tyr and acylated by an acyl group having 15 or less carbon atoms, preferably 7 or less, e.g. acetyl for purposes of producing equivalent CRF agonists, certain of which are suitable for radioiodination and use in screening assays. In addition, instead of the simple amide at the C-terminus, a lower alkyl-substituted amide, e.g. 1–4 carbon atoms, i.e. methylamide, ethylamide, etc, may be incorporated. The amino group which is reacted to form the 30–33 lactam cyclizing bond or the α-amino group of one of the residues in positions 30 through 33 may be alkylated, as by adding a methyl group; such changes are considered to create equivalent cyclic peptides. As described hereinbefore, the lactam linkage between the side chains of the residues in the 30- and 33-positions is preferred; however, biopotency is also increased, but to a somewhat lessor degree, by alternative cyclizing linkages in this same region of the molecule. For example, the side chain of Glu$^{28}$ or Glu$^{29}$ can be linked respectively to Lys$^{31}$ or Lys$^{32}$, or instead respectively to Lys$^{32}$ or Lys$^{33}$ (creating a one-residue longer span). These somewhat less biopotent alternatives are considered to be equivalents to the 30–33 cyclizing linkage. Likewise when a D- or L-isomer of Aph, Lys, Orn, Dbu, Dpr, Arg, or Agl is present in the 32-position, its side chain amino group may be optionally alkylated by methyl or ethyl. All such aforementioned equivalent peptides are considered as being within the scope of the invention.

SEQUENCE LISTING SUMMARY

SEQ ID NO:1, when the C-terminus is amidated, is the amino acid sequence of ovine CRF.

SEQ ID NO:2, when the C-terminus is amidated, is the amino acid sequence of rat/human CRF.

SEQ ID NO:3, when pGlu is at the N-terminus and the C-terminus is amidated, is the amino acid sequence of frog sauvagine.

SEQ ID NO:4, when the C-terminus is amidated, is the amino acid sequence of α-helical CRF, referred to as "AHC".

SEQ ID NO:5, when the C-terminus is amidated, is the amino acid sequence of porcine CRF.

SEQ ID NO:6, when the C-terminus is amidated, is the amino acid sequence of bovine CRF.

SEQ ID NO:7, when the C-terminus is amidated, is the amino acid sequence of fish CRF.

SEQ ID NO:8, when the C-terminus is amidated, is the amino acid sequence of carp urotensin.

SEQ ID NO:9, when the C-terminus is amidated, is the amino acid sequence of suckerfish urotensin.

SEQ ID NO:10, when the C-terminus is amidated, is the amino acid sequence of flathead (Maggy) sole urotensin.

SEQ ID NO:11, when the C-terminus is amidated, is the amino acid sequence of flounder urotensin.

What is claimed is:

1. A cyclic 35-residue CRF agonist peptide having the formula:

(cyclo 30–33)Y$_1$-Ser-R$_8$-Asp-R$_{10}$-R$_{11}$-D-Phe-R$_{13}$-R$_{14}$-R$_{15}$-Arg-R$_{17}$-R$_{18}$-R$_{19}$-R$_{20}$-R$_{21}$-R$_{22}$-R$_{23}$-R$_{24}$-R$_{25}$-R$_{26}$-R$_{27}$-R$_{28}$-R$_{29}$-Glu-R$_{31}$-R$_{32}$-R$_{33}$-R$_{34}$-Arg-R$_{36}$-R$_{37}$-R$_{38}$-R$_{39}$-R$_{40}$-R$_{41}$-NH$_2$ wherein $Y_1$ is an acyl group having not more than 15 carbon atoms; $R_8$ is Leu or Ile; $R_{10}$ is Leu or CML; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, CML, Nle or Met; $R_{19}$ is CML, Leu or Ile; $R_{20}$ is Glu, D-Glu, Cys or His; $R_{21}$ is Nle, Leu, CML or Met; $R_{22}$ is Ala, D-Ala, Aib, Thr, Asp or Glu; $R_{23}$ is Arg, Cys, Orn or Lys; $R_{24}$ is Ala, Gln, Ile, Asn, CML or Aib; $R_{25}$ is Asp or Glu; $R_{26}$ is Gln, Asn or Lys; $R_{27}$ is CML, Glu, Gln or Leu; $R_{28}$ is Ala, Lys, Arg or Aib; $R_{29}$ is Gln, Aib or Glu; $R_{31}$ is Aib or an L-isomer of a natural α-amino acid other than Cys; $R_{32}$ is Aib; $R_{33}$ is Lys or Orn; $R_{34}$ is Asn or Aib; $R_{36}$ is Lys, Orn, Arg, Har, CML or Leu; $R_{37}$ is CML, Leu, Nle or Tyr; $R_{38}$ is Nle, Met, CML or Leu; $R_{39}$ is Glu, Aib or Asp; $R_{40}$ is Ile, Aib, CML, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Phe may be substituted by Phe, Leu, Tyr, D-Leu, D-Tyr, D-Cpa, D-Trp, D-Nal, D-Pal or another D-isomer α-amino acid; provided that a second cyclizing bond may exist between $R_{20}$ and $R_{23}$.

2. A CRF agonist peptide according to claim 1 having the formula:

(cyclo 30–33)Y$_1$-Ser-R$_8$-Asp-Leu-R$_{11}$-D-Phe-His-R$_{14}$-Leu-Arg-Glu-R$_{18}$-Leu-R$_{20}$-Nle-R$_{22}$-R$_{23}$-Ala-R$_{25}$-Gln-Leu-Ala-R$_{29}$-Glu-Ala-R$_{32}$-R$_{33}$-R$_{34}$-Arg-R$_{36}$-R$_{37}$-Nle-R$_{39}$-R$_{40}$-NH$_2$ wherein $Y_1$ is an acyl group having not more than 7 carbon atoms; $R_8$ is Leu or Ile; $R_{11}$ is Thr or Ser; $R_{14}$ is Leu or CML; $R_{18}$ is Val, Nle, CML or Met; $R_{20}$ is Glu or D-Glu; $R_{22}$ is Ala or Thr; $R_{23}$ is Arg or Lys; $R_{25}$ is Asp or Glu; $R_{29}$ is Gln or Glu; $R_{32}$ is Aib; $R_{33}$ is Lys or Orn; $R_{34}$ is Asn or Aib; $R_{36}$ is Lys or Leu; $R_{37}$ is Leu or CML; $R_{39}$ is Glu or Asp; $R_{40}$ is Ile, CML or Glu; and $R_{41}$ is Ile, Aib or Ala; wherein Phe may be substituted for D-Phe.

3. A CRF agonist peptide according to claim 1 wherein $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

4. A CRF agonist peptide according to claim 1 having the formula:

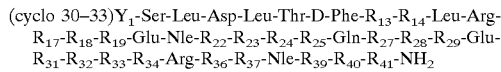

wherein $Y_1$ is a acyl group having not more than 7 carbon atoms; $R_{13}$ is His or Tyr; $R_{14}$ is Leu or CML; $R_{17}$ is Glu or CML; $R_{18}$ is Val, CML, Nle or Met; $R_{19}$ is Leu or CML; $R_{22}$ is Ala, Aib or Thr; $R_{23}$ is Arg or Lys; $R_{24}$ is Ala or Aib; $R_{25}$ is Asp or Glu; $R_{27}$ is Leu, CML or Glu; $R_{28}$ is Ala or Aib; $R_{29}$ is Gln, Aib or Glu; $R_{31}$ is Ala or Aib; $R_{32}$ is Aib; $R_{33}$ is Lys or Orn; $R_{34}$ is Asn or Aib; $R_{36}$ is Lys, CML or Leu; $R_{37}$ is CML or Leu; $R_{39}$ is Glu, Aib or Asp; $R_{40}$ is Ile, Aib, CML or Glu; and $R_{41}$ is Ala, Aib, CML or Ile; and wherein D-Phe may be substituted by Phe, D-Tyr, D-Cpa, D-Nal or D-Pal.

5. A CRF agonist peptide according to claim 1 having the formula, or a nontoxic salt thereof:

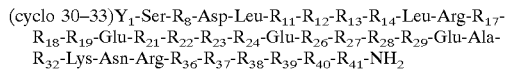

wherein $Y_1$ is an acyl group having not more than 7 carbon atoms; $R_8$ is Leu or Ile; $R_{11}$ is Thr or Ser; $R_{12}$ is D-Phe or D-Leu; $R_{13}$ is His or Glu; $R_{14}$ is Leu or CML; $R_{17}$ is Glu, Lys or Asn; $R_{18}$ is Val, CML or Nle; $R_{19}$ is Leu or Ile; $R_{21}$ is Nle or Ile; $R_{22}$ is Ala or Glu; $R_{23}$ is Arg or Lys; $R_{24}$ is Ala, Asn, Gln or Ile; $R_{26}$ is Gln, Asn or Lys; $R_{27}$ is Leu, CML, Glu or Gln; $R_{28}$ is Ala, Arg or Lys; $R_{29}$ is Gln or Glu; $R_{32}$ is Aib; $R_{36}$ is Lys, Arg, CML or Leu; $R_{37}$ is Leu, CML or Tyr; $R_{38}$ is Nle or Leu; $R_{39}$ is Glu or Asp; $R_{40}$ is Ile, Thr, CML or Glu; and $R_{41}$ is Ala, Ile, CML or Val.

6. A composition for stimulating secretion of ACTH and β-END-LI in mammals comprising an effective amount of a CRF agonist peptide or a nontoxic addition salt thereof in accordance with claim 1 and a pharmaceutically or veterinarily acceptable liquid or solid carrier therefor.

7. A CRF agonist peptide according to claim 1 having the formula, or a nontoxic salt thereof:

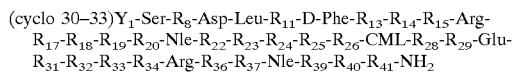

wherein $Y_1$ is an acyl group having not more than 7 carbon atoms; $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is D-Glu or Glu; $R_{22}$ is Ala, D-Ala, Aib, Thr, Asp or Glu; $R_{23}$ is Arg or Lys; $R_{24}$ is Ala, CML or Aib; $R_{25}$ is Asp or Glu; $R_{26}$ is Gln, Asn or Lys; $R_{28}$ is Ala or Aib; $R_{29}$ is Gln, Aib or Glu; $R_{31}$ is Ala or Aib; $R_{32}$ is Aib; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Leu or Phe or Leu may be substituted for D-Phe.

8. A CRF agonist peptide according to claim 7 wherein $R_{33}$ is Lys and wherein at least one of $R_{14}$, $R_{18}$, $R_{37}$, and $R_{40}$ is CML.

9. A CRF agonist peptide according to claim 7 having the formula:

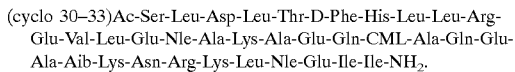

10. A CRF agonist peptide according to claim 1 having the formula:

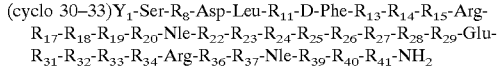

wherein $Y_1$ is an acyl group having not more than 7 carbon atoms; $R_8$ is Leu or Ile; $R_{11}$ is Thr or Ser; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is D-Glu or Glu; $R_{22}$ is Ala, D-Ala, Aib, Thr, Asp or Glu; $R_{23}$ is Arg or Lys; $R_{24}$ is Ala or Aib; $R_{25}$ is Asp or Glu; $R_{26}$ is Gln, Asn or Lys; $R_{27}$ is Leu or CML; $R_{28}$ is Ala or Aib; $R_{29}$ is Gln, Aib or Glu; $R_{31}$ is Ala or Aib; $R_{32}$ is Aib; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Ala, Val, Leu, Nle, Phe, Nva, Gly or Gln; and $R_{41}$ is Ala, Aib, Ile, CML, Gly, Val, Leu, Nle, Phe, Nva or Gln; wherein D-Leu or Phe or Leu may be substituted for D-Phe.

11. A cyclic CRF agonist peptide according to claim 10 having the formula:

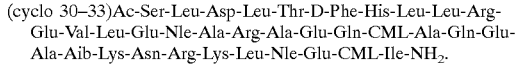

12. A cyclic 35-residue CRF agonist peptide having the formula:

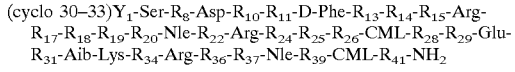

wherein $Y_1$ is an acyl group having not more than 15 carbon atoms; $R_8$ is Leu or Ile; $R_{10}$ is Leu or CML; $R_{11}$ is Thr or Ser; $R_{13}$ is His, Tyr or Glu; $R_{14}$ is CML or Leu; $R_{15}$ is CML or Leu; $R_{17}$ is Glu, CML, Asn or Lys; $R_{18}$ is Val, CML, Nle or Met; $R_{19}$ is CML, Leu or Ile; $R_{20}$ is Glu, D-Glu or His; $R_{22}$ is Ala, D-Ala, Aib, Thr, Asp or Glu; $R_{24}$ is Ala, Gln, Ile, Asn, CML or Aib; $R_{25}$ is Asp or Glu; $R_{26}$ is Gln, Asn or Lys; $R_{28}$ is Ala, Lys, Arg or Aib; $R_{29}$ is Gln, Aib or Glu; $R_{31}$ is Aib or an L-isomer of a natural α-amino acid other than Cys; $R_{34}$ is Asn or Aib; $R_{36}$ is Lys, Orn, Arg, Har, CML or Leu; $R_{37}$ is CML, Leu, Nle or Tyr; $R_{39}$ is Glu, Aib or Asp; and $R_{41}$ is Ala, Aib, Ile, CML, Gly, Val, Leu, Nle, Phe, Nva or Gln.

* * * * *

UNITED STATES PATENT AND TRADEMARK OFFICE
CERTIFICATE OF CORRECTION

PATENT NO. : 6,326,463 B1
DATED : December 4, 2001
INVENTOR(S) : Rivier

It is certified that error appears in the above-identified patent and that said Letters Patent is hereby corrected as shown below:

<u>Column 1,</u>
After line 8, insert, as an initial paragraph:

-- This invention was made with Government support under Grant No. DK-26741 awarded by the National Institutes of Health. The Government has certain rights in this invention. --

Signed and Sealed this

Thirtieth Day of July, 2002

*Attest:*

*Attesting Officer*

JAMES E. ROGAN
*Director of the United States Patent and Trademark Office*

SEQUENCE LISTING

```
(1) GENERAL INFORMATION (iii) NUMBER OF SEQUENCES: 11

(2) INFORMATION FOR SEQ ID NO:1:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:1:

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
                20                  25                  30

Ser Asn Arg Lys Leu Leu Asp Ile Ala
```

```
                35                  40

(2) INFORMATION FOR SEQ ID NO:2:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:2:

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
            35                  40

(2) INFORMATION FOR SEQ ID NO:3:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:3:

Ser Gln Glu Pro Pro Ile Ser Leu Asp Leu Thr Phe His Leu Leu Arg
1               5                   10                  15

Glu Met Leu Glu Met Ala Lys Ala Glu Gln Glu Ala Glu Gln Ala Ala
            20                  25                  30

Leu Asn Arg Leu Leu Leu Glu Glu Ala
            35                  40

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:4:

Ser Gln Glu Pro Pro Ile Ser Leu Asp Leu Thr Phe His Leu Leu Arg
1               5                   10                  15

Glu Val Leu Ala Met Thr Lys Ala Asp Gln Leu Ala Gln Gln Ala His
            20                  25                  30

Ser Asn Arg Lys Leu Leu Asp Ile Ala
            35                  40

(2) INFORMATION FOR SEQ ID NO:5:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:5

Ser Gln Glu Pro Pro Ile Ser Leu Asp Leu Thr Phe His Leu Leu Arg
1               5                   10                  15
```

```
Glu Val Leu Glu Met Thr Lys Ala Asp Gln Leu Ala Gln Gln Ala His
            20                  25                  30

Ser Asn Arg Lys Leu Leu Ala Ile Ala
            35                  40

(2) INFORMATION FOR SEQ ID NO:6:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:6:

Ser Gln Glu Pro Pro Ile Ser Leu Asp Leu Thr Phe His Leu Leu Arg
1               5                   10                  15

Glu Val Leu Ala Met Thr Lys Ala Asp Gln Leu Ala Gln Gln Ala His
            20                  25                  30

Ser Asn Arg Lys Leu Leu Ala Ile Ala
            35                  40

(2) INFORMATION FOR SEQ ID NO:7:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:7:

Ser Glu Glu Pro Pro Ile Ser Leu Asp Leu Thr Phe His Leu Leu Arg
1               5                   10                  15

Glu Val Leu Ala Met Ala Arg Ala Glu Gln Leu Ala Gln Gln Ala His
            20                  25                  30

Ser Asn Arg Lys Leu Met Glu Ile Ile
            35                  40

(2) INFORMATION FOR SEQ ID NO:8:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:8:

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Ala Ile Ile
            35                  40

(2) INFORMATION FOR SEQ ID NO:9:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide
```

(xi) SEQUENCE DESCRIPTION: SEQ ID NO:9:

Ser Xaa Glu Pro Pro Ile Ser Leu Asp Leu Thr Xaa His Leu Leu Arg
1               5                   10                  15

Glu Val Leu Xaa Xaa Xaa Xaa Xaa Gln Leu Ala Gln Gln Ala Xaa
            20              25                  30

Ser Asn Arg Xaa Leu Xaa Xaa Ile Xaa
        35              40

(2) INFORMATION FOR SEQ ID NO:10:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:10:

Xaa Xaa Xaa Xaa Pro Ile Ser Xaa Xaa Leu Xaa Xaa Xaa Xaa Leu Arg
1               5                   10                  15

Xaa Xaa Xaa Xaa Xaa Xaa Xaa Xaa Xaa Xaa Xaa Xaa Gln Ala Xaa
            20              25                  30

Xaa Asn Arg Xaa Xaa Xaa Xaa Xaa Xaa
        35              40

(2) INFORMATION FOR SEQ ID NO:11:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:11:

Ser Xaa Glu Pro Pro Ile Ser Leu Xaa Leu Thr Xaa Xaa Xaa Leu Arg
1               5                   10                  15

Glu Xaa Leu Xaa Xaa Ala Lys Xaa Glu Gln Xaa Ala Glu Gln Ala Xaa
            20              25                  30

Xaa Xaa Arg Xaa Xaa Xaa Xaa Xaa Xaa
        35              40